US012670985B1

(12) United States Patent (10) Patent No.: US 12,670,985 B1
Menzie, Jr. et al. (45) Date of Patent: Jun. 30, 2026

(54) AUTOMATED HEALTHCARE STAFFING

(71) Applicant: Sanford Health, Sioux Falls, SD (US)

(72) Inventors: Robert Menzie, Jr., Sioux Falls, SD (US); Emily Buckingham-Carlson, Fargo, ND (US)

(73) Assignee: Sanford Health, Sioux Falls, SD (US)

( * ) Notice: Subject to any disclaimer, the term of this patent is extended or adjusted under 35 U.S.C. 154(b) by 1170 days.

(21) Appl. No.: 17/580,034

(22) Filed: Jan. 20, 2022

Related U.S. Application Data

(60) Provisional application No. 63/139,681, filed on Jan. 20, 2021.

(51) Int. Cl.
| | |
|---|---|
| *G16H 40/20* | (2018.01) |
| *G06N 3/0442* | (2023.01) |
| *G06N 3/045* | (2023.01) |
| *G06N 3/049* | (2023.01) |
| *G06Q 10/0631* | (2023.01) |
| *G16H 50/20* | (2018.01) |

(52) U.S. Cl.
CPC ............. *G16H 40/20* (2018.01); *G06N 3/045* (2023.01); *G06N 3/049* (2013.01); *G06Q 10/06311* (2013.01); *G16H 50/20* (2018.01); *G06N 3/0442* (2023.01)

(58) Field of Classification Search
CPC ........ G16H 40/20; G16H 50/20; G06N 3/045; G06N 3/049; G06N 3/0442; G06Q 10/06311
USPC ......................................................... 705/2–3
See application file for complete search history.

(56) References Cited

U.S. PATENT DOCUMENTS

| | | | | |
|---|---|---|---|---|
| 2016/0314256 A1* | 10/2016 | Su | ............................ | G16H 50/50 |
| 2018/0261319 A1* | 9/2018 | Bowie | .................... | G16H 40/20 |
| 2020/0311652 A1* | 10/2020 | Morin | .................... | G06N 20/20 |

OTHER PUBLICATIONS

D. Ahmed,Z., Mohamed,K., Zeeshan,S. and Dong, X. Artificial intelligence with multi-functional machine learning platform development for better healthcare and precision medicine. Database (2020) vol. 2020: article ID baaa010; doi:10.1093/database/baaa010 (Year: 2020).*

* cited by examiner

*Primary Examiner* — Amber A Misiaszek
(74) *Attorney, Agent, or Firm* — McDonnell Boehnen Hulbert & Berghoff LLP

(57) ABSTRACT

Improved methods are provided for predicting health system census over months or years and for incorporating such predictions into practitioner work schedules and predicted future practitioner needs. These improved methods permit users to interact with the predictive methods, allowing intuition and lateral goals to be conveniently incorporated into iterative updates of the predictions. These improved methods allow 'big data' predictive methods to be combined with human intuition by presenting users with human-interpretable adjustments to the predictor. The effects of user-selected modifications to underlying predictions and/or assumptions can be injected into the improved predictors and the effects of the modification presented back to the user, allowing the user to see the effects of various human-selected changes to hiring, admission, or other healthcare practices on long-term patient care.

21 Claims, 8 Drawing Sheets

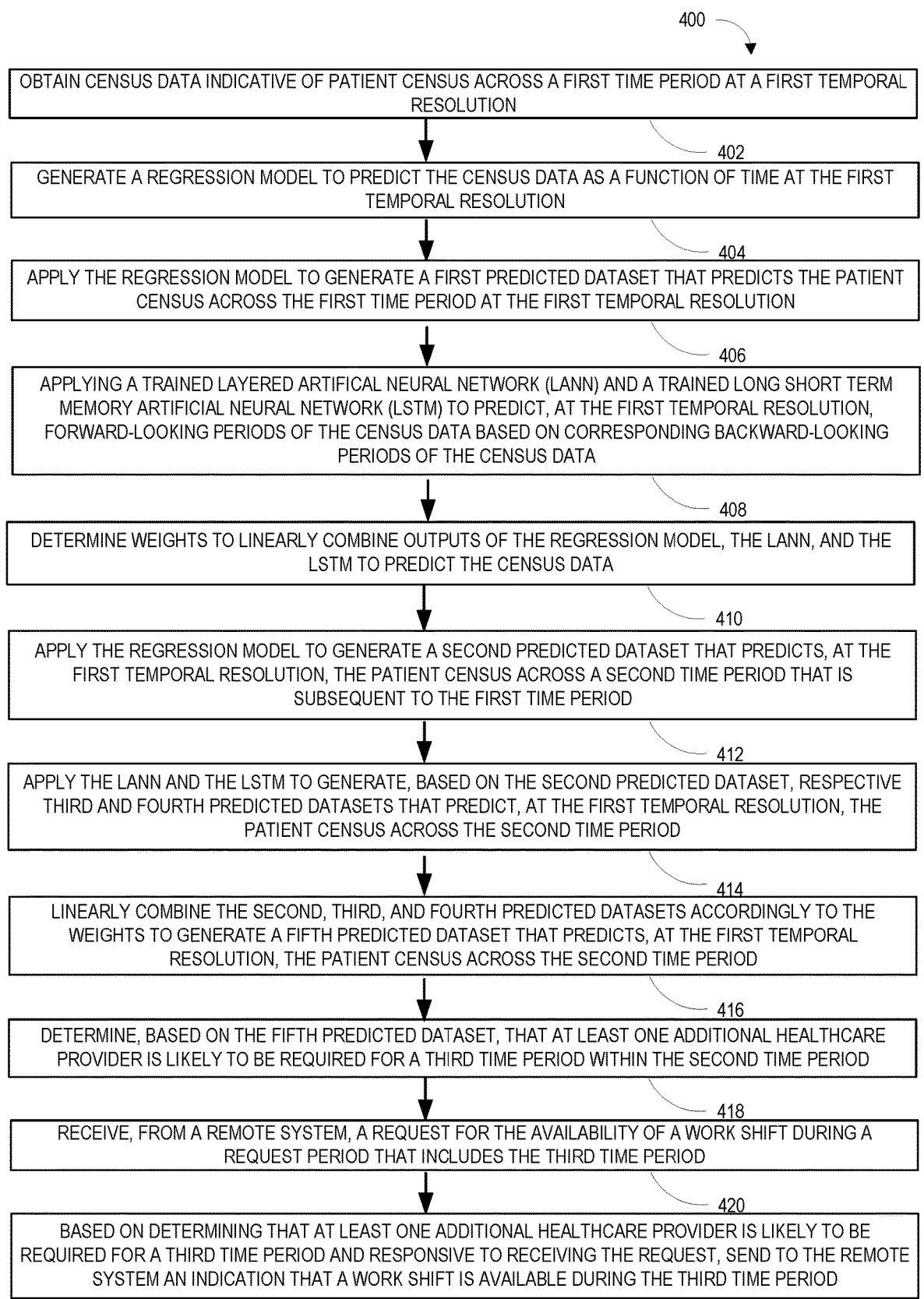

400

OBTAIN CENSUS DATA INDICATIVE OF PATIENT CENSUS ACROSS A FIRST TIME PERIOD AT A FIRST TEMPORAL RESOLUTION

402

GENERATE A REGRESSION MODEL TO PREDICT THE CENSUS DATA AS A FUNCTION OF TIME AT THE FIRST TEMPORAL RESOLUTION

404

APPLY THE REGRESSION MODEL TO GENERATE A FIRST PREDICTED DATASET THAT PREDICTS THE PATIENT CENSUS ACROSS THE FIRST TIME PERIOD AT THE FIRST TEMPORAL RESOLUTION

406

APPLYING A TRAINED LAYERED ARTIFICAL NEURAL NETWORK (LANN) AND A TRAINED LONG SHORT TERM MEMORY ARTIFICIAL NEURAL NETWORK (LSTM) TO PREDICT, AT THE FIRST TEMPORAL RESOLUTION, FORWARD-LOOKING PERIODS OF THE CENSUS DATA BASED ON CORRESPONDING BACKWARD-LOOKING PERIODS OF THE CENSUS DATA

408

DETERMINE WEIGHTS TO LINEARLY COMBINE OUTPUTS OF THE REGRESSION MODEL, THE LANN, AND THE LSTM TO PREDICT THE CENSUS DATA

410

APPLY THE REGRESSION MODEL TO GENERATE A SECOND PREDICTED DATASET THAT PREDICTS, AT THE FIRST TEMPORAL RESOLUTION, THE PATIENT CENSUS ACROSS A SECOND TIME PERIOD THAT IS SUBSEQUENT TO THE FIRST TIME PERIOD

412

APPLY THE LANN AND THE LSTM TO GENERATE, BASED ON THE SECOND PREDICTED DATASET, RESPECTIVE THIRD AND FOURTH PREDICTED DATASETS THAT PREDICT, AT THE FIRST TEMPORAL RESOLUTION, THE PATIENT CENSUS ACROSS THE SECOND TIME PERIOD

414

LINEARLY COMBINE THE SECOND, THIRD, AND FOURTH PREDICTED DATASETS ACCORDINGLY TO THE WEIGHTS TO GENERATE A FIFTH PREDICTED DATASET THAT PREDICTS, AT THE FIRST TEMPORAL RESOLUTION, THE PATIENT CENSUS ACROSS THE SECOND TIME PERIOD

416

DETERMINE, BASED ON THE FIFTH PREDICTED DATASET, THAT AT LEAST ONE ADDITIONAL HEALTHCARE PROVIDER IS LIKELY TO BE REQUIRED FOR A THIRD TIME PERIOD WITHIN THE SECOND TIME PERIOD

418

RECEIVE, FROM A REMOTE SYSTEM, A REQUEST FOR THE AVAILABILITY OF A WORK SHIFT DURING A REQUEST PERIOD THAT INCLUDES THE THIRD TIME PERIOD

420

BASED ON DETERMINING THAT AT LEAST ONE ADDITIONAL HEALTHCARE PROVIDER IS LIKELY TO BE REQUIRED FOR A THIRD TIME PERIOD AND RESPONSIVE TO RECEIVING THE REQUEST, SEND TO THE REMOTE SYSTEM AN INDICATION THAT A WORK SHIFT IS AVAILABLE DURING THE THIRD TIME PERIOD

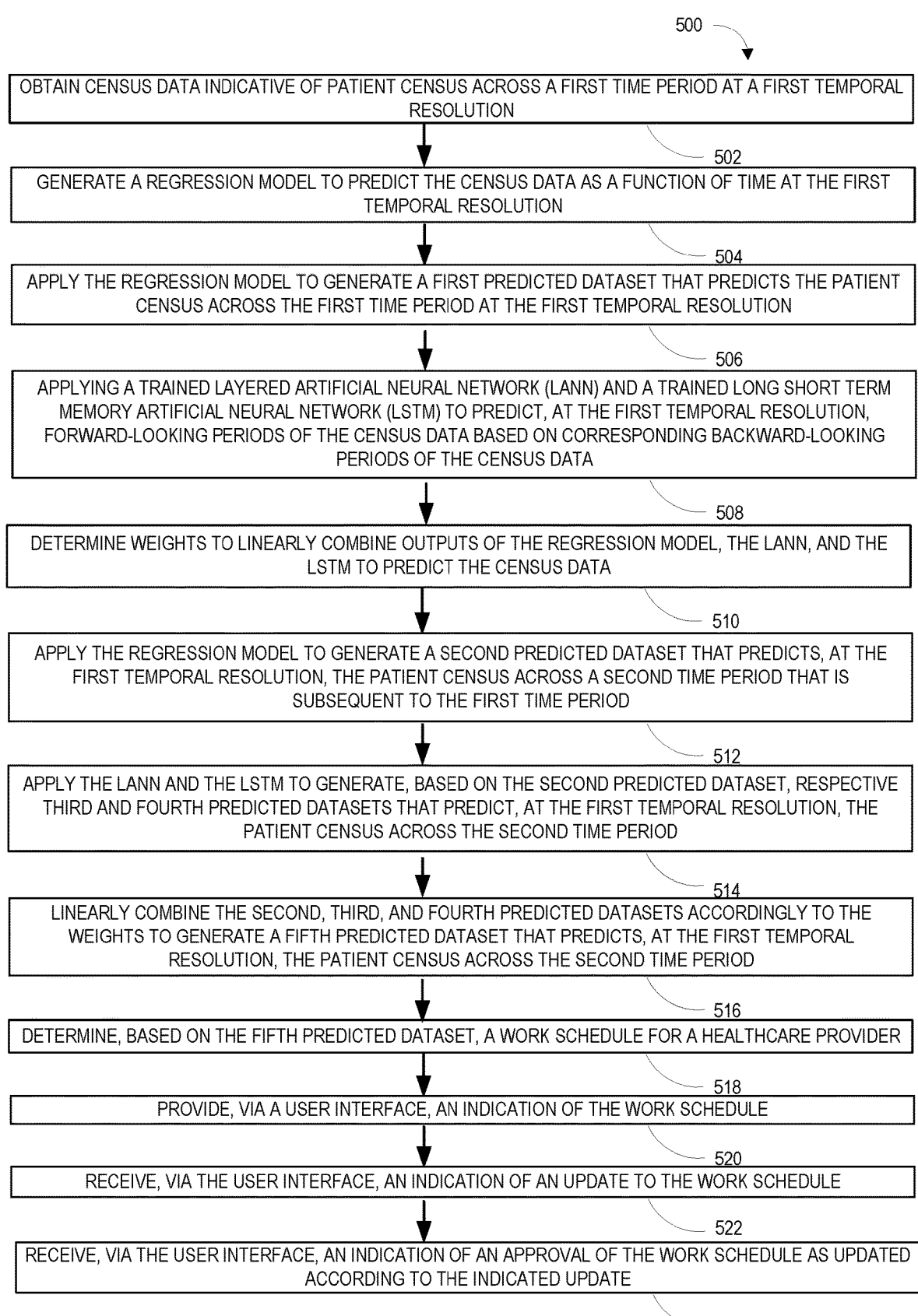

500

OBTAIN CENSUS DATA INDICATIVE OF PATIENT CENSUS ACROSS A FIRST TIME PERIOD AT A FIRST TEMPORAL RESOLUTION

502

GENERATE A REGRESSION MODEL TO PREDICT THE CENSUS DATA AS A FUNCTION OF TIME AT THE FIRST TEMPORAL RESOLUTION

504

APPLY THE REGRESSION MODEL TO GENERATE A FIRST PREDICTED DATASET THAT PREDICTS THE PATIENT CENSUS ACROSS THE FIRST TIME PERIOD AT THE FIRST TEMPORAL RESOLUTION

506

APPLYING A TRAINED LAYERED ARTIFICIAL NEURAL NETWORK (LANN) AND A TRAINED LONG SHORT TERM MEMORY ARTIFICIAL NEURAL NETWORK (LSTM) TO PREDICT, AT THE FIRST TEMPORAL RESOLUTION, FORWARD-LOOKING PERIODS OF THE CENSUS DATA BASED ON CORRESPONDING BACKWARD-LOOKING PERIODS OF THE CENSUS DATA

508

DETERMINE WEIGHTS TO LINEARLY COMBINE OUTPUTS OF THE REGRESSION MODEL, THE LANN, AND THE LSTM TO PREDICT THE CENSUS DATA

510

APPLY THE REGRESSION MODEL TO GENERATE A SECOND PREDICTED DATASET THAT PREDICTS, AT THE FIRST TEMPORAL RESOLUTION, THE PATIENT CENSUS ACROSS A SECOND TIME PERIOD THAT IS SUBSEQUENT TO THE FIRST TIME PERIOD

512

APPLY THE LANN AND THE LSTM TO GENERATE, BASED ON THE SECOND PREDICTED DATASET, RESPECTIVE THIRD AND FOURTH PREDICTED DATASETS THAT PREDICT, AT THE FIRST TEMPORAL RESOLUTION, THE PATIENT CENSUS ACROSS THE SECOND TIME PERIOD

514

LINEARLY COMBINE THE SECOND, THIRD, AND FOURTH PREDICTED DATASETS ACCORDINGLY TO THE WEIGHTS TO GENERATE A FIFTH PREDICTED DATASET THAT PREDICTS, AT THE FIRST TEMPORAL RESOLUTION, THE PATIENT CENSUS ACROSS THE SECOND TIME PERIOD

516

DETERMINE, BASED ON THE FIFTH PREDICTED DATASET, A WORK SCHEDULE FOR A HEALTHCARE PROVIDER

518

PROVIDE, VIA A USER INTERFACE, AN INDICATION OF THE WORK SCHEDULE

520

RECEIVE, VIA THE USER INTERFACE, AN INDICATION OF AN UPDATE TO THE WORK SCHEDULE

522

RECEIVE, VIA THE USER INTERFACE, AN INDICATION OF AN APPROVAL OF THE WORK SCHEDULE AS UPDATED ACCORDING TO THE INDICATED UPDATE

APPLY A FIRST STOCHASTIC SIMULATOR TO GENERATE, BASED ON A SET OF CENSUS SIMULATION PARAMETERS THAT INCLUDES AT LEAST A PATIENT ADMISSION RATE PARAMETER THAT VARIES ACROSS A PERIOD OF TIME, A FIRST PLURALITY OF SIMULATED TIME-VARYING PATIENT CENSUSES ACROSS THE PERIOD OF TIME, WHEREIN APPLYING THE FIRST STOCHASTIC SIMULATOR COMPRISES SIMULATING THE ENTRY AND EXIT OF PATIENTS INTO AND OUT OF AT LEAST ONE DEPARTMENT OF A HEALTHCARE FACILITY

600

602

APPLY A SECOND STOCHASTIC SIMULATOR TO GENERATE, BASED ON A SET OF STAFF SIMULATION PARAMETERS, A FIRST PLURALITY OF SIMULATED TIME-VARYING AVAILABLE STAFF COUNTS ACROSS THE PERIOD OF TIME, WHEREIN APPLYING THE SECOND STOCHASTIC SIMULATOR COMPRISES SIMULATING THE ENTRY AND EXIT OF STAFF INTO AND OUT OF THE AT LEAST ONE DEPARTMENT OF THE HEALTHCARE FACILITY

604

BASED ON THE FIRST PLURALITY OF SIMULATED TIME-VARYING PATIENT CENSUSES, THE FIRST PLURALITY OF SIMULATED TIME-VARYING PATIENT CENSUSES, AND A SET OF DEPARTMENT STAFFING CONSTRAINTS, DETERMINE, ACROSS THE PERIOD OF TIME, AT LEAST ONE OF A TIME-VARYING SHIFT RUN RATE, A TIME-VARYING DIFFERENCE BETWEEN PREDICTED AND REQUIRED CORE STAFF AVAILABILITY, OR A TIME-VARYING DIFFERENCE BETWEEN PREDICTED AND REQUIRED FLOAT STAFF AVAILABILITY

606

DISPLAY, VIA A USER INTERFACE, THE DETERMINED AT LEAST ONE OF A TIME-VARYING SHIFT RUN RATE, A TIME-VARYING DIFFERENCE BETWEEN PREDICTED AND REQUIRED CORE STAFF AVAILABILITY, OR A TIME-VARYING DIFFERENCE BETWEEN PREDICTED AND REQUIRED FLOAT STAFF AVAILABILITY

608

RECEIVE, VIA THE USER INTERFACE, AT LEAST ONE UPDATED PARAMETER VALUE, WHEREIN THE UPDATED PARAMETER VALUE COMPRISES AN UPDATE TO AT LEAST ONE OF: AT LEAST ONE UPDATED PARAMETER OF THE SET OF CENSUS SIMULATION PARAMETERS, AT LEAST ONE UPDATED PARAMETER OF THE SET OF STAFF SIMULATION PARAMETERS, OR AT LEAST ONE UPDATED CONSTRAINT OF THE SET OF DEPARTMENT STAFFING CONSTRAINTS

610

USING THE AT LEAST ONE UPDATED PARAMETER VALUE, (I) APPLY THE FIRST STOCHASTIC SIMULATOR AND THE SECOND STOCHASTIC SIMULATOR TO GENERATE A SECOND PLURALITY OF SIMULATED TIME-VARYING PATIENT CENSUSES ACROSS THE PERIOD OF TIME AND A SECOND PLURALITY OF SIMULATED TIME-VARYING AVAILABLE STAFF COUNTS ACROSS THE PERIOD OF TIME, RESPECTIVELY, AND (II), BASED AT LEAST ON THE SECOND PLURALITY OF SIMULATED TIME-VARYING PATIENT CENSUSES AND THE SECOND PLURALITY OF SIMULATED TIME-VARYING PATIENT CENSUSES, DETERMINE, ACROSS THE PERIOD OF TIME, AT LEAST ONE OF AN UPDATED TIME-VARYING SHIFT RUN RATE, AN UPDATED TIME-VARYING DIFFERENCE BETWEEN PREDICTED AND REQUIRED CORE STAFF AVAILABILITY, OR AN UPDATED TIME-VARYING DIFFERENCE BETWEEN PREDICTED AND REQUIRED FLOAT STAFF AVAILABILITY

612

DISPLAY, VIA THE USER INTERFACE, THE DETERMINED AT LEAST ONE OF AN UPDATED TIME-VARYING SHIFT RUN RATE, AN UPDATED TIME-VARYING DIFFERENCE BETWEEN PREDICTED AND REQUIRED CORE STAFF AVAILABILITY, OR AN UPDATED TIME-VARYING DIFFERENCE BETWEEN PREDICTED AND REQUIRED FLOAT STAFF AVAILABILITY

AUTOMATED HEALTHCARE STAFFING

CROSS-REFERENCE TO RELATED APPLICATION

The present application is a non-provisional patent application claiming priority to U.S. Provisional Patent Application No. 63/139,681, filed on Jan. 20, 2021, the contents of which are hereby incorporated by reference.

BACKGROUND

It can be difficult to accurately predict staffing needs for a hospital or other healthcare department or facility. Accurate prediction can allow for reductions in costs while maintaining patient care and coverage levels by more efficiently allocating staff to periods when patient census is higher. Such an allocation can include determining how many permanent nursing staff (or "core" nurses) or other permanent staff to hire, and when, as well as determining how many temporary nursing staff to contract with, and when. Central to accurately predicting staffing needs is accurately predicting patient census from day to day and within days for months or even years in advance. The more accurate and the farther out patient census can be predicted, the better a healthcare facility can preemptively adjust its staffing to maintain patient care levels while minimizing the cost (in salary, benefits, or other costs) of that care. Such an improved allocation of staff can also reduce burnout and improve staff health and morale while also reducing overtime costs.

SUMMARY

In a first aspect, a method is provided that includes: (i) obtaining census data indicative of patient census across a first time period at a first temporal resolution; (ii) generating a regression model to predict the census data as a function of time at the first temporal resolution; (iii) applying the regression model to generate a first predicted dataset that predicts the patient census across the first time period at the first temporal resolution; (iv) applying a trained layered artificial neural network (LANN) and a trained long short term memory artificial neural network (LSTM) to predict, at the first temporal resolution, forward-looking periods of the census data based on corresponding backward-looking periods of the census data; (v) determining weights to linearly combine outputs of the regression model, the LANN, and the LSTM to predict the census data; (vi) applying the regression model to generate a second predicted dataset that predicts, at the first temporal resolution, the patient census across a second time period that is subsequent to the first time period; (vii) applying the LANN and the LSTM to generate, based on the second predicted dataset, respective third and fourth predicted datasets that predict, at the first temporal resolution, the patient census across the second time period; (viii) linearly combining the second, third, and fourth predicted datasets according to the weights to generate a fifth predicted dataset that predicts, at the first temporal resolution, the patient census across the second time period; (ix) determining, based on the fifth predicted dataset, that at least one additional healthcare provider is likely to be required for a third time period within the second time period; (x) receiving, from a remote system, a request for the availability of a work shift during a request period that includes the third time period; and (xi) based on determining that at least one additional healthcare provider is likely to be required for a third time period and responsive to receiving the request, sending to the remote system an indication that a work shift is available during the third time period.

In a second aspect, a method is provided that includes: (i) obtaining census data indicative of patient census across a first time period at a first temporal resolution; (ii) generating a regression model to predict the census data as a function of time at the first temporal resolution; (iii) applying the regression model to generate a first predicted dataset that predicts the patient census across the first time period at the first temporal resolution; (iv) applying a trained layered artificial neural network (LANN) and a trained long short term memory artificial neural network (LSTM) to predict, at the first temporal resolution, forward-looking periods of the census data based on corresponding backward-looking periods of the census data; (v) determining weights to linearly combine outputs of the regression model, the LANN, and the LSTM to predict the census data; (vi) applying the regression model to generate a second predicted dataset that predicts, at the first temporal resolution, the patient census across a second time period that is subsequent to the first time period; (vii) applying the LANN and the LSTM to generate, based on the second predicted dataset, respective third and fourth predicted datasets that predict, at the first temporal resolution, the patient census across the second time period; (viii) linearly combining the second, third, and fourth predicted datasets accordingly to the weights to generate a fifth predicted dataset that predicts, at the first temporal resolution, the patient census across the second time period; (ix) determining, based on the fifth predicted dataset, a work schedule for a healthcare provider; (x) providing, via a user interface, an indication of the work schedule; (xi) receiving, via the user interface, an indication of an update to the work schedule; and (xii) receiving, via the user interface, an indication of an approval of the work schedule as updated according to the indicated update In a third aspect, a method is provided that includes: (i) applying a first stochastic simulator to generate, based on a set of census simulation parameters that includes at least a patient admission rate parameter that varies across a period of time, a first plurality of simulated time-varying patient censuses across the period of time, wherein applying the first stochastic simulator comprises simulating the entry and exit of patients into and out of at least one department of a healthcare facility; (ii) applying a second stochastic simulator to generate, based on a set of staff simulation parameters, a first plurality of simulated time-varying available staff counts across the period of time, wherein applying the second stochastic simulator comprises simulating the entry and exit of staff into and out of the at least one department of the healthcare facility; (iii) based on the first plurality of simulated time-varying patient censuses, the first plurality of simulated time-varying patient censuses, and a set of department staffing constraints, determining, across the period of time, at least one of a time-varying shift run rate, a time-varying difference between predicted and required core staff availability, or a time-varying difference between predicted and required float staff availability; (iv) displaying, via a user interface, the determined at least one of a time-varying shift run rate, a time-varying difference between predicted and required core staff availability, or a time-varying difference between predicted and required float staff availability; (v) receiving, via the user interface, at least one updated parameter value, wherein the updated parameter value comprises an update to at least one of: at least one updated parameter of the set of census simulation parameters, at least one updated parameter of the set of staff simulation parameters, or at least one updated constraint of the set of department staffing constraints; (vi) using the at least one updated parameter value. (a) applying the first stochastic simulator and the second stochastic simulator to generate a second plurality of simulated time-varying patient censuses across the period of time and a second plurality of simulated time-varying available staff counts across the period of time, respectively, and (b), based at least on the second plurality of simulated time-varying patient censuses and the second plurality of simulated time-varying patient censuses, determining, across the period of time, at least one of an updated time-varying shift run rate, an updated time-varying difference between predicted and required core staff availability, or an updated time-varying difference between predicted and required float staff availability; and (vii) displaying, via the user interface, the determined at least one of an updated time-varying shift run rate, an updated time-varying difference between predicted and required core staff availability, or an updated time-varying difference between predicted and required float staff availability In another aspect an article of manufacture is provided that includes a non-transitory computer-readable medium, having stored therein instructions executable by a computing device to cause the computing device to perform any one or more of the above methods.

In another aspect a system is provided that includes: (i) one or more processors; and (ii) a non-transitory computer-readable medium, having stored therein instructions executable by the one or more processors to cause the system to perform any one or more of the above methods.

These as well as other aspects, advantages, and alternatives will become apparent to those of ordinary skill in the art by reading the following detailed description with reference where appropriate to the accompanying drawings. Further, it should be understood that the description provided in this summary section and elsewhere in this document is intended to illustrate the claimed subject matter by way of example and not by way of limitation.

BRIEF DESCRIPTION OF THE FIGURES

FIG. 4 illustrates an example method.

FIG. 5 illustrates an example method.

FIG. 6 illustrates an example method.

DETAILED DESCRIPTION

Examples of methods and systems are described herein. It should be understood that the words "exemplary," "example," and "illustrative," are used herein to mean "serving as an example, instance, or illustration." Any embodiment or feature described herein as "exemplary," "example," or "illustrative," is not necessarily to be construed as preferred or advantageous over other embodiments or features. Further, the exemplary embodiments described herein are not meant to be limiting. It will be readily understood that certain aspects of the disclosed systems and methods can be arranged and combined in a wide variety of different configurations.

As used herein, the singular forms "a", "an" and "the" include plural referents unless the context clearly dictates otherwise. "And" as used herein is interchangeably used with "or" unless expressly stated otherwise.

All embodiments of any aspect of the disclosure can be used in combination, unless the context clearly dictates otherwise.

I. OVERVIEW

It can be difficult to accurately predict staffing needs for a hospital or other healthcare department or facility. Accurate prediction can allow for reductions in costs while maintaining patient care and coverage levels by more efficiently allocating staff to periods when patient census is higher. Such an allocation can include determining how many permanent nursing staff (or "core" nurses) or other permanent staff to hire, and when, as well as determining how many temporary nursing staff to contract with, and when. Central to accurately predicting staffing needs is accurately predicting patient census from day to day and within days for months or even years in advance. The more accurate and the farther out patient census can be predicted, the better a healthcare facility can preemptively adjust its staffing to maintain patient care levels while minimizing the cost (in salary, benefits, or other costs) of that care. Such an improved allocation of staff can also reduce burnout and improve staff health and morale while also reducing overtime costs.

The predictive methods described herein provide significant improvements in long-term patient census prediction and in optimizing staffing based on that improved prediction. These methods are able to achieve 80-95% accuracy (5-20% mean absolute percentage error) in predicting nurse staffing needs at an hourly resolution over a predictive window of a year. Such high accuracy over long time windows allows for improved determinations about hiring permanent nursing or other healthcare staff. Such high accuracy can also allow the hiring or scheduling processes to be automated, or partially automated. Such high accuracy can additionally allow contracting or hiring of temporary nursing staff (or "float" nurses) to be performed in an automated manner, e.g., as part of an automated nurse matching service or app.

Figure 1:
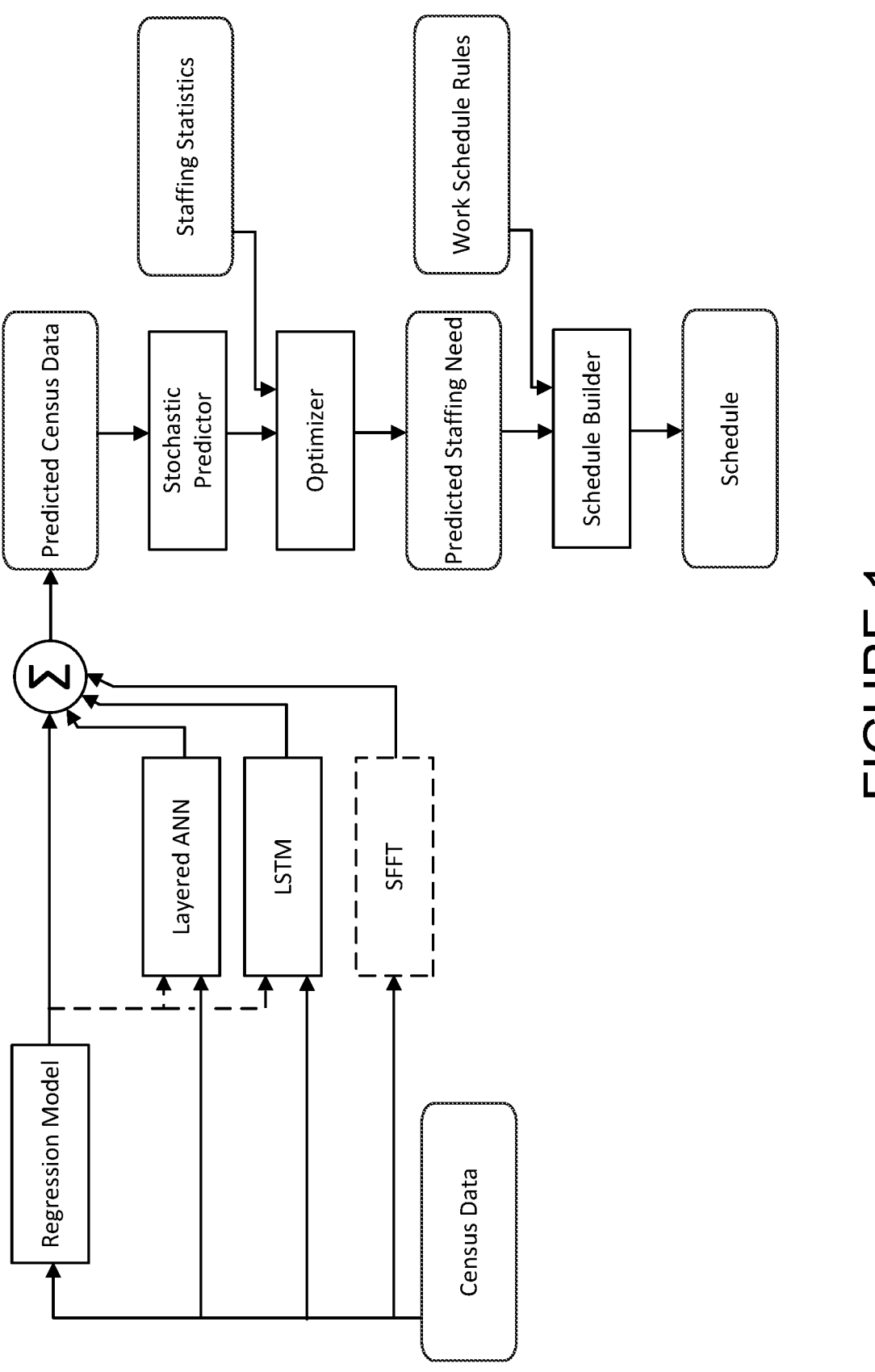
FIG. 1 is a flowchart illustrating aspects of a method for patient load prediction and staff scheduling, according to an example embodiment.

FIG. 1 depicts elements of an improved method for accurately predicting patient census ("Predicted Census Data") at high temporal resolution over long periods of time based on high-temporal-resolution historical census data ("Census Data"). Such a prediction can also be augmented using historical admit, discharge and transfer (ADT) data. FIG. 1 also depicts elements of an improved method for determining staffing levels ("Predicted Staffing Need") to service a patient population based on the predicted patient census and for determining a schedule ("Schedule") for individual existing, future, or temporary ("float") staff.

The historical census data is used as an input, and as training data, for a regression model, a layered artificial neural network ("Layered ANN," e.g., a convolutional neural network (CNN) or a stacked residual network), a long short-term memory recurrent neural network ("LSTM"), and a Short Fast Fourier Transform ("SFFT"). Their outputs are linearly combined (">," according to weights that have been set, based on the historical census data, in a manner that will be described in greater detail below) to generate the predicted census data. The Layered ANN and LSTM have been trained based on the historical census data. Parameters of the regression model have also been set based on the historical census data.

Note that certain elements of the predictive model may be omitted (indicated by dashed lines). In particular, the SFFT may be omitted, and presentation of the output of the regression model as an input to the layered ANN and LSTM may be omitted (i.e., one or both of the layered ANN and LSTM may receive only the historical census data as an input). Omission of the SFFT, use of a CNN as the layered ANN, and providing the output of the regression model as an input to both the CNN and LSTM result in 80-95% accuracy (5-20% mean absolute percentage error) in predicting nurse staffing needs at an hourly resolution over a predictive window of a year. Addition of the SFFT, use of a stacked residual network for the layered ANN, and providing the historical census data only as input to the LSTM and stacked residual network (that is, not providing the output of the regression model as an input to the layered ANN and LSTM) results in an additional 4% improvement in predictive accuracy.

The regression model is structured to predict the historical census data as a function of time at a set temporal resolution (e.g., at an hourly resolution) that may be the same temporal resolution as the historical patient census data. The regression model may be or include a variety of statistical time-series regression or prediction algorithms, e.g., the FB-prophet time-series predictive model or some other variety of generalized additive model. The regression model can include one or more terms related to overall trends in the patient census (e.g., a linear or nonlinear term to represent non-cyclical increase or decrease in patient census from year to year over time). The regression model can also include a number of terms related to time within a year, within a season, within a month, within a week, within a day, whether a date is a holiday, whether a date is a specific holiday, and/or according to some other repeating timeline. For example, the regression model could predict the patient census on Monday, May 25, 2020 from 4-5 PM based on a combination (e.g., a sum) of terms related to the date being a Monday, to the date being within the month of May, to the date being the $25^{th}$ of the month, to the date being the $146^{th}$ day of the year, to the date being a holiday, to the date being Memorial Day, to the date being within the season of Spring, to the time of day being the $17^{th}$ hour of the day, to the time of day being in the afternoon, and/or to the time of day being during the first shift. Such terms could be linearly or nonlinearly combined to result in the output of the regression model.

The layered ANN and LSTM can receive as inputs a specified duration of "prior" patient census data (or "backward-looking" periods of patient census data). These models may also optionally receive as inputs corresponding predictions thereof generated by the regression model. The layered ANN and LSTM then output predictions for the patient census for a specified duration subsequent to the input data (or "forward-looking" periods of census data). The duration of the forward- and backward-looking periods could be the same or differ between the layered ANN and LSTM and/or between the forward and backward periods. For example, the forward- and backward-looking periods for both the layered ANN and the LSTM could have durations of one week, or approximately one week (e.g., between five days and nine days).

Because the period of the forward-looking periods of census data predicted by the layered ANN and LSTM may be less than the period of total census data predicted (e.g., one week being less than a full year), a repeated or "feedback" process can be used to generate the full duration of predicted census data. This method will be described by way of example assuming that the forward- and backward-looking periods have durations of one week, but other durations are possible. Such a feedback process can include using the historical census data to predict a first week of future census data by combining the outputs of the regression model, layered ANN, LSTM, and optionally SFFT according to the determined weights. To do so, the layered ANN and LSTM receive as inputs the final week of the historical census data as well as, optionally, the regression model's prediction thereof. To predict the second week of future census data, the predicted first week of future census data is applied as an input to the layered ANN and LSTM, optionally along with the regression model's prediction of the first week of future census data (using the combined prediction of the first week of future census data as "historical census data" for the purposes of input to the layered ANN and LSTM). The outputs of the layered ANN and LSTM for the second week are then combining with the output of the regression model and optionally the SFFT for the second week according to the determined weights to predict the second week of future census data. This process is then repeated to predict an entire year or other duration of future census data (e.g., using the combined prediction of the second week of census data as an input to the layered ANN and LSTM to generate their predicted components of the third week of future census data, etc.).

The historical census data can be used to train or otherwise configure the regression model, layered ANN, LSTM, and stochastic predictor (in examples wherein the stochastic predictor includes a stochastic neural network or other train-able stochastic predictive model). The data could be high-temporal-resolution historical patient census data, e.g., having a resolution at the per-shift level of three or more times per day or even higher resolution. For example, the historical census data could have a resolution greater than twelve times per day, e.g., an hourly resolution. The forward- and backward-looking time periods of data used to train the layered ANN, LSTM, and/or stochastic NN could be locked to discrete steps, e.g., each forward-looking time period and each backward-looking time period could be a Sunday-Saturday time period or a Monday-Sunday time period.

The duration of historical census data used could be selected to allow for sufficient training information to arrive at accurate predictions while avoiding over-fitting and/or fitting to 'out of date' historical data that represents patterns of patient census that are no longer relevant. For example, the duration of the historical census data used in the methods described herein could be between three and four years long. The improved accuracy of 80-95% accuracy (5-20% mean absolute percentage error) in predicting nurse staffing needs at an hourly resolution was obtained by using as training input between three and four years of historical census data.

Generating the regression model (which may also be referred to as "training" the regression model) can include a variety of processes. Weights, parameters, or other configuration information for the regression model could be determined, based on the historical census data, using analytical formulas (e.g., formulas to determine the maximum likelihood values for the parameters). Additionally or alternatively, gradient descent or other iterative methods could be used to set parameters of the regression model, e.g., to reduce a least-squares or other cost function evaluated between the historical census data and the regression models' prediction thereof. Training of the layered ANN and LSTM can then be performed using the historical census data and optionally the 'trained' regression model's prediction thereof. A variety of methods for training a neural network based on such training data may be applied. Once the outputs for the regression model, layered ANN, LSTM, and optionally SFFT have been generated, weights for the combination of those outputs can then be generated, e.g., to reduce a least-squares difference between the weight-combined outputs and the actual historical census data. In another example, the different outputs could be combined based on their respective models respective relative accuracy as predicting the census data over a previous period of forward predictions, e.g., over the prior year of forward predictions.

Once the future patient census has been predicted, this prediction can be used to determine staffing needs over the predicted period of time (e.g., 105 days). This can include predicting the need for multiple different types of staff, e.g., permanently hired nursing staff (or "core" staff), whose hiring and termination may include longer and more involved processes, and temporarily contracted nursing staff (or "float" staff), who may be hired on a temporary basis (e.g., weekly). Determining such staffing needs may include optimizing a cost function that includes a variety of factors, which may include salary and other costs of employment, costs related to overtime payment in order to service patient load when needed, "effective costs" related to understaffing when patient load outstrips the ability to compensate with overtime, temporary staff, or other means, and/or other factors. Predicting staffing needs can include determining the levels of different varieties of staff at different temporal resolutions. For example, permanent "core" staff levels could be predicted at a shift-level resolution (e.g., more then twice per week) while temporary "float" staff levels could be predicted at week-level resolution (e.g., more than twice per month).

While it is possible to predict staffing need ("Predicted Staffing Need") and/or to generate work schedules for one or more healthcare workers ("Schedule") based directly on the predicted census data, such a method may fail to take into account the variability of patient census from that prediction. Accordingly, FIG. 1 also depicts a method for predicting staffing need while also predicting and taking into account such variability. This method include using a stochastic predictor ("Stochastic Predictor") to generate, from the predicted census data, a plurality of different possible patterns of census data and/or statistical distributions of the possible pattern of census data. An optimization algorithm ("Optimizer") can then generate predictions of the level of needed staff ("Predicted Staffing Need," which may be broken up into permanent "core" and temporary "float" staff levels) using the generated plurality of 'possible' patterns of census data and/or census statistical information in combination with information about patterns of staff leave (sick leave, FMLA, PTO, etc.), quitting or retirement, or other information about the variation of the existing or future staff during the predicted time period. As noted above, this optimization can include reducing a cost function that include optimizing a cost function that includes a variety of factors (e.g., salary and other costs of employment, overtime costs, "effective costs" related to understaffing). Such an optimization process could include reducing an expected level of such a cost function across the population of stochastically-generated possible patterns of census data, reducing a maximum level of such a cost function across the population of possible patterns of census data (reducing the severity of a 'worst case scenario') and/or ensuring that such a maximum level is less than a specified maximum level, and/or addressing some other objective or factor.

The stochastic predictor ("Stochastic Predictor") generates, based on the input predicted census data, a probabilistic version of the predicted census data. Such a stochastic predictor could take a number of different forms. For example, the stochastic predictor could output a predicted mean, variance, upper and lower quintiles, or other data related to the predicted distribution of the predicted census over time. Additionally or alternatively, the stochastic predictor could output a plurality of sets of stochastically-generated census time series predictions over the window of prediction (e.g., 50-2000 predicted trajectories of census predictions across the prediction window). The stochastic predictor could be a trained stochastic neural net. Additionally or alternatively, the stochastic predictor could include a census simulator as described below (e.g., in connection with FIG. 2 or 3A) to simulate the movement of patients into, out of, and between departments of a healthcare facility or system, based on the predicted census data (e.g., trends of growth in the census data). Such a simulator could be run a number of times (e.g., 50-2000 times) to generate a plurality of simulated census time series over the prediction window. Such a set of predicted census time series could then be applied to the optimizer (e.g., as a set of predicted time series and/or as a set of distributions, averages with variances, or some other summary statistics over time) to generate predicted staffing need ("Predicted Staffing Need").

Some or all of the processes depicted in relation to FIG. 1 could be performed repeatedly as additional actual patient census data is obtained. For example, the prediction of census data, prediction of staffing need, and/or healthcare worker schedules could be re-computed as additional patient data is obtained (e.g., as the patient census data is generated from admissions, discharges, etc.). Such re-calculation could be performed as the updated patient census data is obtained (e.g., on an hourly basis) or according to some other schedule (e.g., once per week). Such re-calculation could be performed using the same regression model, layered ANN, LSTM, SFFT, weights, stochastic predictor, and/or other elements as were used to generate the original prediction. Alternatively, some or all of those elements may be re-trained based on the updated patient census data.

Once the staffing need has been predicted, a smartphone app, online service, or other automated functionality could be employed to identify new "core" staff for hire, to set up contracts or schedules with "float" staff, or to implement some other action to put actual facility staffing levels in accord with the predicted staffing need. For example, a nurse could, via a user interface of a smartphone app or a website on a personal computer or smartphone, request a work shift or other employment across a period of time (e.g., one or more work shifts within a particular day, one or more days or weeks of temporary "float" work). The request could be sent to a server or other system that maintains and/or generates the predicted staffing need data along with data about existing or scheduled staffing resources. The server could then, based on that information, respond to the request with an indication of whether shift(s) or other amounts of staffing are needed during the requested period. The nurse could then accept one or more of the indicated available shifts(s). Such an acceptance could then result in the nurse being put on the official work schedule, contracted to work temporarily for one or more weeks, or some other employment result.

The staffing need and/or schedule data could be updated over time, either due to updating the predicted patient census and/or due to healthcare workers quitting, being hired, accepting shifts, or other changes to the schedule. In such examples, the information sent to a nurse in response to a request could change from one request to the next. So, for example, a first request for shift availability during a particular week could receive a response of 'no availability', while a second request some time later (e.g., several days later) could receive a response of 'shift(s) available' (or vice versa). Additionally or alternatively, such updated availability changes could be pushed to a smartphone app or an alert sent in some other manner (e.g., via email). Such alerts could be sent in response to a user explicitly requesting such alerts and/or in response to a request for availability for a particular time that later becomes available.

The predicted staffing need could also be used to generate work schedules for individual healthcare workers. FIG. 1 depicts aspects of such a process ("Schedule Builder") generating a work schedule ("Schedule") for a nurse or other healthcare worker using the predicted staffing need as well as a variety of scheduling rules ("Work Schedule Rules") which may include rules about shift length, shift timing, overtime utilization, minimum staff levels, maximum staff levels, required staff (e.g., a requirement that at least one staff member qualified to perform certain tasks, or having been certified in some manner, be present on every shift), or other rules. Such an automatically-generated schedule could then be sent to the healthcare worker (e.g., via an email) and/or made available in response to a request. Alternatively, an automatically-generated schedule could be presented to a manager or other individual for modification and/or approval prior to being made available to the healthcare worker. In examples wherein the staffing need and/or schedule data is updated over time, the schedule made available to a healthcare worker (e.g., via email or in response to a request) could change over time (e.g., from one request to the next. In such examples, the ability of the schedule to change could be indicated as part of the schedule (e.g., "NON-FINAL," or "Prospective Schedule").

The above methods for predicting, applying, and interacting with patient census data provide a variety of benefits. However, the configuration of their predictive elements (e.g., machine learning models) are generally non-interpretable or not intuitively understandable by a human mind. It is desirable, then, to augment these relatively opaque predictive methods with additional methods that include human-interpretable aspects (e.g., elements that simulate different aspects of the operation of a healthcare system). This provides the benefits of the 'big data' predictive methods described above while also opening up the predictive process to human interaction, thus allowing a human user to manipulate the human-interpretable elements of the predictive simulation model (e.g., number of beds in a department, rate of hiring of new staff, retention of existing staff). This human manipulation of the model parameters allows a user to 'test' changes to hiring, facility development, and treatment policies by changing the parameters and then re-running the simulation, allowing the user to observe corresponding predicted changes in patient census, staff counts, and other related outcomes. Since these additional simulation methods are based on the above predictive methods, they allow a user to combine their intuition and knowledge of the simulated department or healthcare facility with the improved-accuracy 'big data' predictions provided by the methods described elsewhere herein.

Figure 2:
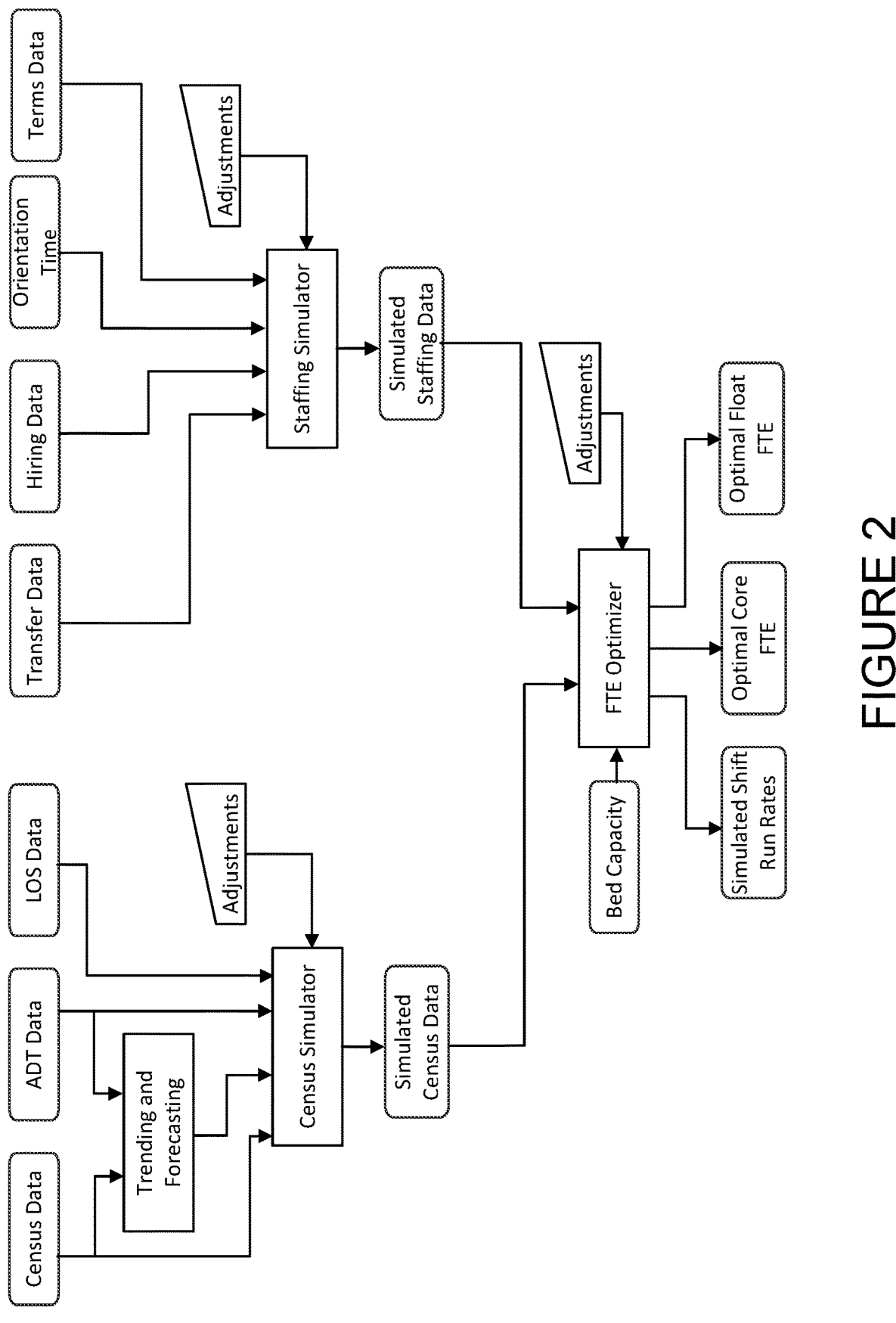
FIG. 2 is a flowchart illustrating aspects of a method for patient load simulation, staff hiring process simulation, and staff load prediction, according to an example embodiment.

FIG. 2 depicts elements of an example of such an improved mechanistic stochastic simulator. The method includes a stochastic simulator to predict patient census ("Census Simulator") over time in one or more departments of a healthcare facility and a stochastic simulator to predict available staff counts ("Staffing Simulator") over time in the one or more departments of the healthcare facility. The predicted staff could be nurses or some other variety of healthcare facility staff. These stochastic simulators generate respective simulation data for patient census ("Simulated Census Data") and available staff ("Simulated Staffing Data") that are then applied to an optimizer ("FTE Optimizer") to determine how many total/additional staff are likely to be needed across the simulated time period. This predicted staffing output can include predicting the likely total/additional needed shift run rates ("Simulated Shift Run Rates"), fulltime hires ("Optimal Core FTE"), and/or temporary contract hires ("Optimal Float FTE").

The simulated census and staffing data are generated by repeatedly performing the respective simulations, with variations from performance to performance being caused by the stochastic nature of the simulation (e.g., using a Poisson distribution, based on predicted patient admit rates, to randomly or pseudo-randomly generate an integer count of newly admitted patients for each hour, shift, day, or other temporal resolution of the simulation). To generate each set of simulated data, the respective stochastic simulator could be run a specified number of times, e.g., 50-2000 times, in order generate a plurality of simulated time-varying patient censuses/staffing counts over the time period being simulated. These sets of simulated censuses/counts could then be provided to the FTE optimizer as-is (e.g., the FTE optimizer could generate a respective plurality of runs of core/float staff shortfall/excess, and then determine averages therefrom) and/or time-varying averages, deviations, or other parameters of the distribution of census/staff count across time could be determined from the sets of simulated census/counts and provided to the FTE optimizer.

The FTE optimizer could receive, as inputs, the bed capacity of each department under simulation ("Bed Capacity") as well as a number of other factors in order to generate outputs. Parameters used by the FTE optimizer, in addition to the input simulated census and staff count data and bed capacity, could include rules about overtime, FMLA use, unpaid time off, paid time off, requirements for shift duration/timing, cost of core staff, cost to hire core staff, cost of temporary staff, availability of temporary staff, and manually set and/or historically observed parameters related thereto (e.g., observed rates, timing, and duration of PTO use, observed rates and duration of FMLA use, etc.). The FTE optimizer could be, itself, a stochastic simulator in that it could include a stochastic, mechanical model for use of PTO, FMLA, etc. by staff in order to simulate, based on input simulated staff counts, simulated "effective" available number of full-time equivalents over time and, from this "effective" count to determine optimal totals and/or increases/decreases in core and float staff levels or other information related to staffing and/or patient care.

The census simulator receives, as inputs, historical census data ("Census Data"), historical data about admissions, discharges, and transfers into, out of, and between departments of the healthcare facility ("ADT Data," e.g., probability of a patient entering, leaving, or transferring into/out of a department), data about the length of stay of patients in one or more departments of the healthcare facility ("LOS Data," e.g., mean times of patient stays from admission/transfer in to discharge/transfer out), and/or other data. The historical and/or ADT data are also applied to a predictor ("Trending and Forecasting"), e.g., a predictor as described in connection with FIG. 1, to generate a time-varying patient admission rate into one or more departments, in order that the simulation can reflect predicted changes in patient admits and/or other factors of the simulation (e.g., number of beds in each department). The output of this prediction module could include, e.g., a constant or time-varying rate of change in the admission rate to the department(s) of the healthcare facility over the time period being simulated by the simulator. The patient census simulator could be configured in a variety of ways to take such parameters as inputs and to output, via stochastic means, a simulated time-varying patient census for one or more departments of a healthcare system. For example, the patient census simulator could be configured as depicted in FIG. 3A.

The available staff count simulator receives, as inputs, data about transfers between departments within the healthcare facility ("Transfer Data," e.g., the rate of transfer to/from pairs of departments within the healthcare facility, which may be dependent on the staff count for one or both of the relevant departments, data about mean time from admission/transfer into a department until transfer out), data about hiring new staff ("Hiring Data," e.g., probability of onboarding new staff, total local availability of new staff, dependence of new staff hiring on number of open positions), data about training new staff ("Orientation Time," which can include the time to train new staff as well as other information, e.g., probability of newly hired staff completing training), data about staff quitting or being terminated from a department ("Terms Data," e.g., mean or other distribution of time from hiring/transfer in to quitting/termination and/or a rate of spontaneous quitting/termination that may be dependent on staff counts), and/or other input parameters. The available staff count simulator could be configured in a variety of ways to take such parameters as inputs and to output, via stochastic means, a simulated time-varying level of available staff for one or more departments of a healthcare system. For example, the available staff count simulator could be configured as depicted in FIG. 3B.

Figures 3A, 3B:
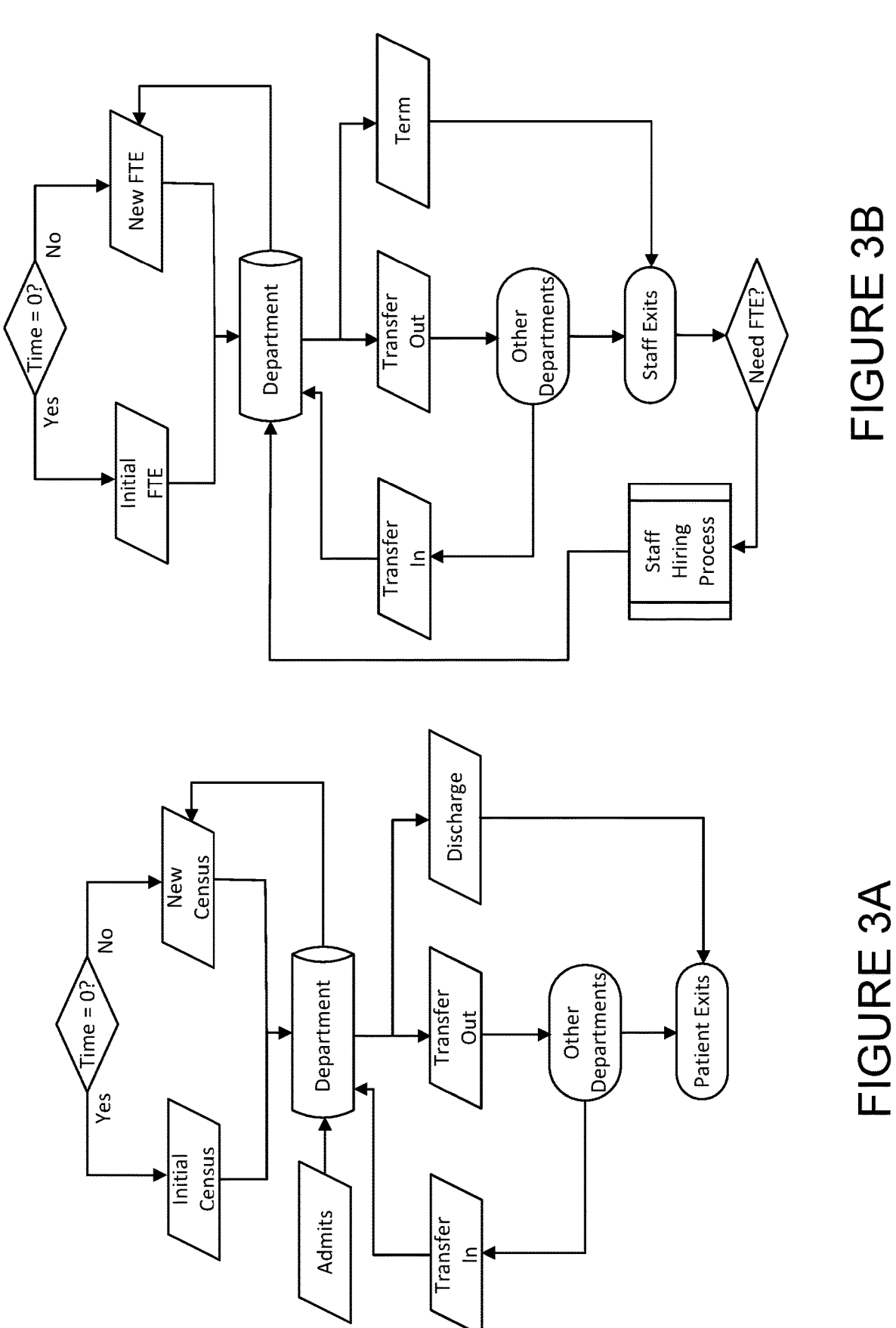
FIG. 3A is a flowchart illustrating aspects of a method for patient load simulation, according to an example embodiment.
FIG. 3B is a flowchart illustrating aspects of a method for staff hiring process simulation, according to an example embodiment.

FIG. 3A illustrates aspects of a stochastic simulator for generating simulated runs of time-varying patient censuses across extended periods of time (e.g., one year, 3 years, 5 years). In particular, FIG. 3A depicts aspects of a method for generating, based on an input patient census ("Initial Census" or "New Census") for a first time point (e.g., a first day, a first shift, a first hour) for a particular department ("Department") of a healthcare system, a patient census for a subsequent time point (e.g., the next day, the next shift, the next hour) for the particular department. The method includes adding, to the previous time point's census ("Initial Census" for the first time point to be predicted, the "New Census" output from the previous iteration of the method otherwise) a stochastically-generated number of newly admitted patients ("Admits") and a stochastically-generated number of patients transferred in ("Transfer In") from other department(s) in the healthcare system ("Other Departments"), subtracting a stochastically-generated number of patients transferred out ("Transfer Out") to the other department(s), and subtracting a stochastically-generated number of patients being discharged from the healthcare system from the particular department ("Discharge"). The depicted stochastic simulation can be performed, for each time step across a specified period of time, for each one of a number of different departments within a healthcare system in order to generate respective different simulated time-varying patient censuses for each of the departments. In some examples, the total number of patients in a particular department could be capped (e.g., to a constant number of beds, or to a number of beds that changes over time, e.g., according to a predicted trend in overall patient census, according to a development plan, or according to some other factors).

A particular number of patients being "stochastically generated" includes generating the number of patients via a random or pseudo-random process. For example, a Poisson distribution could be sampled to generate the number of newly admitted patients, number of patients transferred in, number of patients transferred out, etc. The parameters of the distribution could be constant or could be dependent upon simulated factors of the model (e.g., the population of the various simulated departments) and/or on time (e.g., an admit rate that increases over time according to a predicted trend in overall patient census). For example, the mean of the Poisson distribution used to determine how many patients to transfer out from a first department to a second department could be the product of the current census of the first department and a time-invariant transfer rate from the first department to the second department. Such a time-invariant transfer rate could be determined from historical transfer data and/or manually set or adjusted based on user input. In another example, a number of patients discharged and/or transferred could be based on a stochastically-generated length of stay determined for each simulated patient. The length of stay for a particular simulated patient could be determined using a Gaussian distribution whose mean is determined based on historical length of stay (LOS) data and/or manually set or adjusted based on user input.

In yet another example, the mean of the Poisson distribution used to determine how many patients are newly admitted into a particular department could be the product of a time-dependent admission rate for the particular department. Such a time-dependent admission rate could be determined from predicted trends in overall patient census for the particular department and/or manually set or adjusted based on user input. For example, a locally weighted scatterplot smoothing (LOWESS) method or some other trend-determination method (linear regression, polynomial fitting, etc.) could be used to generate a trend curve from the census data predicted using one of the other methods described herein (e.g., a method described in connection with FIG. 1). The extracted trend curve could then be used to determine the time-dependent admission rate across the period of time spanned by the predicted census data and/or subsequent periods of time. This could include extracting a single linear growth trend parameter from the complete LOWESS or other curve fit, a series of growth trend parameters at a plurality of different points along the LOWESS or other curve fit (e.g., the slope of the fitted curve at a plurality of points in time along the fitted curve), or some other method of determining one or more patient admission rates over time based on changes or trends in a predicted overall patient census over time. Additionally or alternatively, manually-set or otherwise-acquired patient admission rates could be used. e.g., for periods of time after a time period spanned by predicted patient census data generated as described elsewhere herein. For example, a method described in connection with FIG. 1 could be used to generate patient admission rates for a first period of time (e.g., a first year) while market reports, user inputs, or other data sources could be used to generate patient admission rates for a second, subsequent period of time (e.g., years two and three of a three-year projection, years two-five of a five-year projection).

FIG. 3B illustrates aspects of a stochastic simulator for generating simulated runs of time-varying available staff counts (e.g., counts of available core nursing staff) across extended periods of time (e.g., one year, 3 years, 5 years). In particular, FIG. 3B depicts aspects of a method for generating, based on an input number of full-time equivalent staff ("Initial FTE" or "New FTE") for a first time point (e.g., a first pay period, a first day, a first shift) for a particular department ("Department") of a healthcare system, a number of full-time equivalent staff for a subsequent time point (e.g., the next pay period, the next day, the next shift) for the particular department. The method includes adding, to the previous time point's available staff count ("Initial FTE" for the first time point to be predicted, the "New FTE" output from the previous iteration of the method otherwise) a stochastically-generated number of newly trained staff ("Staff Hiring Process") and a stochastically-generated number of staff transferred in ("Transfer In") from other department(s) in the healthcare system ("Other Departments"), subtracting a stochastically-generated number of staff transferred out ("Transfer Out") to the other department(s), and subtracting a stochastically-generated number of staff quitting and/or being terminated from the healthcare system from the particular department ("Term"). The depicted stochastic simulation can be performed, for each time step across a specified period of time, for each one of a number of different departments within a healthcare system in order to generate respective different simulated time-available staff counts for each of the departments.

A particular number of available staff being "stochastically generated" includes generating the number of patients via a random or pseudo-random process. For example, a Poisson distribution could be sampled to generate the number of newly hired staff beginning a staff hiring and/or training process, number of staff transferred in, number of staff transferred, out, etc. The parameters of the distribution could be constant or could be dependent upon simulated factors of the model (e.g., the number of available staff of the various simulated departments) and/or on time (e.g., a target hiring rate that increases over time according to a specified trend in predicted staffing need). For example, the mean of the Poisson distribution used to determine how many staff to transfer out from a first department to a second department could be the product of the current number of staff in the first department and a time-invariant staff transfer rate from the first department to the second department. Such a time-invariant staff transfer rate could be determined from historical staffing transfer data and/or manually set or adjusted based on user input. In another example, a number of staff termed and/or transferred could be based on a stochastically-generated length of employment determined for each simulated staff member. The length of employment for a particular simulated staff member could be determined using a Gaussian distribution whose mean is determined based on historical staff turnover data and/or manually set or adjusted based on user input.

In yet another example, the mean of a Poisson distribution could be used to determine how many new staff are hired, relative to a specified target hiring rate, and added to a staff hiring process that, itself, could use stochastic and/or non-stochastic processes to determine how many additional staff, and according to what schedule/delay, are added to the number of available staff in a particular department. The target hiring rate could be constant, could change according to a set schedule over time, and/or could change based on the simulated departure of staff from the particular department. For example, departure of a staff member from the particular department (due to termination and/or transfer to another department) could cause the target hiring rate to be incremented, while successfully hiring a new staff member into the staff hiring process could cause the target hiring rate to be decremented.

As noted above, one of the benefits of the predictive methods described above is that it exposes human-understandable parameters to a user, thus permitting the user to understand "why" certain outcomes may be predicted, and also to manually modify one or more of the parameters to determine, prospectively, the likely outcome of such a change. This allows the user to inject their intuition about the operation of the healthcare facility and/or knowledge about local markets for healthcare, healthcare staff, planned or possible future facility development plans, etc. into the simulation and to "test" potential changes to policy prior to implementation. So, the method of FIG. 2 could be performed once, using available historical data, and the outcomes presented to a user (e.g., via a user interface of a laptop, personal computer, tablet, or other computing device). The user could then provide (e.g., via the same user interface) modifications to one or more of the parameters or inputs to the method ("Adjustments" to the parameters/ inputs of the census simulator, staffing simulator, and/or FTE optimizer), in order to reflect potential or expected future changes to, e.g., hiring policy, retention or compensation policy, scheduling, leave, or overtime policy, healthcare demand, facility growth (e.g., increase in number of beds), or other adjustments to the predictor parameters. The method could then be re-performed, using the adjusted parameters/inputs, and the output of the updated prediction then provided to the user (e.g., via the same user interface).

One benefit of this method for simulation, receipt of user-generated parameter adjustments, and re-simulation is that the effectiveness of specific policy changes (e.g., hiring/ retention policies) can be evaluated directly for their likelihood at addressing a predicted staffing shortfall. The output of a first performance of the method of FIG. 2 can provide information about the timing and number of needed core and/or float staff. However, it is not clear that, e.g., increasing the target number of nurse hires by three will result in correcting a predicted three-nurse staffing shortfall. For example, the probability of hiring new staff, the time to train those staff, the likelihood that those staff complete training, etc. could result in a three-nurse increase in the hiring target still resulting in a one-nurse shortfall, due to training attrition, difficulty in finding new hires, etc. Instead, a user can manually adjust the target hiring rate and/or other parameters (e.g., increased retention parameters/longer term of employment parameters in order to reflect changes in overtime policies and compensation) one or more times to determine the necessary change that is likely to result in correcting a staffing shortfall or satisfying some other constraint (e.g., maintaining a set minimum staff to patient ratio while maintaining total staffing costs within a set budget).

Note that the methods described herein have been depicted as being applied to predict patient census data and, from the predicted census data, to predict healthcare worker staffing needs (e.g., nurses, doctors, physical or occupational therapists, intake administrators, floor nurses, nurse managers, etc.) and schedules related thereto. However, these methods could be applied to determining staffing needs for other workplaces based on some underlying usage statistic. For example, to predict a number of police needed based on number of 911 calls or other requests for police support, to predict a number of EMS units needed based on number of 911 calls or other requests for police support, etc. Indeed, these methods could be used to predict the needed amount of non-staff resources in response to some underlying usage statistic. For example, to predict a number of MRI systems or other diagnostic and/or therapeutic systems based on patient usage counts, to predict power generation needs based on historical usage data, etc.

II. EXAMPLE METHODS

FIG. 4 depicts an example method 400. The method 400 includes obtaining census data indicative of patient census across a first time period at a first temporal resolution (402). The method 400 additionally includes generating a regression model to predict the census data as a function of time at the first temporal resolution (404). The method 400 additionally includes applying the regression model to generate a first predicted dataset that predicts the patient census across the first time period at the first temporal resolution (406). The method 400 additionally includes applying a trained layered artificial neural network (LANN) and a trained long short term memory artificial neural network (LSTM) to predict, at the first temporal resolution, forward-looking periods of the census data based on corresponding backward-looking periods of the census data (and, optionally, the first predicted dataset) (408). The LANN could be a convolutional neural network (CNN) or a recurrent neural network. The method 400 additionally includes determining weights to linearly combine outputs of the regression model, the LANN, and the LSTM to predict the census data (410). The method 400 additionally includes applying the regression model to generate a second predicted dataset that predicts, at the first temporal resolution, the patient census across a second time period that is subsequent to the first time period (412). The method 400 additionally includes applying the LANN and the LSTM to generate, based on the second predicted dataset, respective third and fourth predicted datasets that predict, at the first temporal resolution, the patient census across the second time period (414). The method 400 additionally includes linearly combining the second, third, and fourth predicted datasets accordingly to the weights to generate a fifth predicted dataset that predicts, at the first temporal resolution, the patient census across the second time period (416). The method 400 additionally includes determining, based on the fifth predicted dataset, that at least one additional healthcare provider is likely to be required for a third time period within the second time period (418). The method 400 additionally includes receiving, from a remote system, a request for the availability of a work shift during a request period that includes the third time period (420). The method 400 additionally includes, based on determining that at least one additional healthcare provider is likely to be required for a third time period and responsive to receiving the request, sending to the remote system an indication that a work shift is available during the third time period (422). The method 400) could include additional steps or features. For example, a short fast Fourier transform (SFFT) could be applied in parallel with the LANN (e.g., with a recurrent neural network) and the LSTM, with the output of the SFFT being linearly combined, according to an additional weight, with the outputs of the LSTM. LANN, and regression model to improve the accuracy of prediction of the census data.

FIG. 5 depicts an example method 500. The method 500 includes obtaining census data indicative of patient census across a first time period at a first temporal resolution (502).

The method 500 additionally includes generating a regression model to predict the census data as a function of time at the first temporal resolution (504). The method 500 additionally includes applying the regression model to generate a first predicted dataset that predicts the patient census across the first time period at the first temporal resolution (506). The method 500 additionally includes applying a trained layered artificial neural network (LANN) and a trained long short term memory artificial neural network (LSTM) to predict, at the first temporal resolution, forward-looking periods of the census data based on corresponding backward-looking periods of the census data (and, optionally, the first predicted dataset) (508). The LANN could be a convolutional neural network (CNN) or a recurrent neural network. The method 500 additionally includes determining weights to linearly combine outputs of the regression model, the LANN, and the LSTM to predict the census data (510). The method 500 additionally includes applying the regression model to generate a second predicted dataset that predicts, at the first temporal resolution, the patient census across a second time period that is subsequent to the first time period (512). The method 500 additionally includes applying the LANN and the LSTM to generate, based on the second predicted dataset, respective third and fourth predicted datasets that predict, at the first temporal resolution, the patient census across the second time period (514). The method 500 additionally includes linearly combining the second, third, and fourth predicted datasets accordingly to the weights to generate a fifth predicted dataset that predicts, at the first temporal resolution, the patient census across the second time period (516). The method 500 additionally includes determining, based on the fifth predicted dataset, a work schedule for a healthcare provider (518). The method 500) additionally includes providing, via a user interface, an indication of the work schedule (520)). The method 500 additionally includes receiving, via the user interface, an indication of an update to the work schedule (522). The method 500 additionally includes receiving, via the user interface, an indication of an approval of the work schedule as updated according to the indicated update (524). The method 500 could include additional steps or features. For example, a short fast Fourier transform (SFFT) could be applied in parallel with the LANN (e.g., with a recurrent neural network) and the LSTM, with the output of the SFFT being linearly combined, according to an additional weight, with the outputs of the LSTM. LANN, and regression model to improve the accuracy of prediction of the census data.

FIG. 6 depicts an example method 600. The method 600 includes applying a first stochastic simulator to generate, based on a set of census simulation parameters that includes at least a patient admission rate parameter that varies across a period of time, a first plurality of simulated time-varying patient censuses across the period of time, wherein applying the first stochastic simulator comprises simulating the entry and exit of patients into and out of at least one department of a healthcare facility (602). The method 600 additionally includes applying a second stochastic simulator to generate, based on a set of staff simulation parameters, a first plurality of simulated time-varying available staff counts across the period of time, wherein applying the second stochastic simulator comprises simulating the entry and exit of staff into and out of the at least one department of the healthcare facility (604). The method 600 additionally includes, based on the first plurality of simulated time-varying patient censuses, the first plurality of simulated time-varying patient censuses, and a set of department staffing constraints, determining, across the period of time, at least one of a time-varying shift run rate, a time-varying difference between predicted and required core staff availability, or a time-varying difference between predicted and required float staff availability (606). The method 600 additionally includes displaying, via a user interface, the determined at least one of a time-varying shift run rate, a time-varying difference between predicted and required core staff availability, or a time-varying difference between predicted and required float staff availability (608). The method 600 additionally includes receiving, via the user interface, at least one updated parameter value, wherein the updated parameter value comprises an update to at least one of: at least one updated parameter of the set of census simulation parameters, at least one updated parameter of the set of staff simulation parameters, or at least one updated constraint of the set of department staffing constraints (610). The method 600 additionally includes, using the at least one updated parameter value. (i) applying the first stochastic simulator and the second stochastic simulator to generate a second plurality of simulated time-varying patient censuses across the period of time and a second plurality of simulated time-varying available staff counts across the period of time, respectively, and (ii), based at least on the second plurality of simulated time-varying patient censuses and the second plurality of simulated time-varying patient censuses, determining, across the period of time, at least one of an updated time-varying shift run rate, an updated time-varying difference between predicted and required core staff availability, or an updated time-varying difference between predicted and required float staff availability (612). The method 600 additionally includes displaying, via the user interface, the determined at least one of an updated time-varying shift run rate, an updated time-varying difference between predicted and required core staff availability, or an updated time-varying difference between predicted and required float staff availability (614). The method 600 could include additional steps or features.

III. EXAMPLE MACHINE LEARNING MODELS AND TRAINING THEREOF

A machine learning model as described herein may include, but is not limited to: an artificial neural network (e.g., a herein-described convolutional neural networks, a recurrent neural network, a Bayesian network, a hidden Markov model, a Markov decision process, a logistic regression function, a support vector machine, a suitable statistical machine learning algorithm, and/or a heuristic machine learning system), a support vector machine, a regression tree, an ensemble of regression trees (also referred to as a regression forest), a decision tree, an ensemble of decision trees (also referred to as a decision forest), or some other machine learning model architecture or combination of architectures.

An artificial neural network (ANN) could be configured in a variety of ways. For example, the ANN could include two or more layers, could include units having linear, logarithmic, or otherwise-specified output functions, could include fully or otherwise-connected neurons, could include recurrent and/or feed-forward connections between neurons in different layers, could include filters or other elements to process input information and/or information passing between layers, or could be configured in some other way to facilitate the generation of predicted color palettes based on input images.

An ANN could include one or more filters that could be applied to the input and the outputs of such filters could then be applied to the inputs of one or more neurons of the ANN. For example, such an ANN could be or could include a convolutional neural network (CNN), a Stacked Residual Network, or some other variety of ANN. Convolutional neural networks are a variety of ANNs that are configured to facilitate ANN-based classification or other processing based on images or other large-dimensional inputs whose elements are organized within two or more dimensions. The organization of the ANN along these dimensions may be related to some structure in the input structure (e.g., as relative location within the two-dimensional space of an image can be related to similarity between pixels of the image).

In example embodiments, a CNN includes at least one one-dimensional (or higher-dimensional) filter that is applied to an input; the filtered input is then applied to neurons of the CNN (e.g., of a convolutional layer of the CNN). A set of neurons of a CNN could receive respective inputs that are determined by applying the same filter to an input. Additionally or alternatively, a set of neurons of a CNN could be associated with respective different filters and could receive respective inputs that are determined by applying the respective filter to the input. Such filters could be trained during training of the CNN or could be pre-specified. For example, such filters could represent wavelet filters, center-surround filters, or some other pre-specified filter patterns.

A CNN or other variety of ANN could include multiple convolutional layers (e.g., corresponding to respective different filters and/or features), pooling layers, rectification layers, fully connected layers, or other types of layers. Convolutional layers of a CNN represent convolution of an input (e.g., of a filtered, downsampled, or otherwise-processed version of an input time series of census data), with a filter. Pooling layers of a CNN apply non-linear downsampling to higher layers of the CNN, e.g., by applying a maximum, average, L2-norm, or other pooling function to a subset of neurons, outputs, or other features of the higher layer(s) of the CNN. Rectification layers of a CNN apply a rectifying nonlinear function (e.g., a non-saturating activation function, a sigmoid function) to outputs of a higher layer. Fully connected layers of a CNN receive inputs from many or all of the neurons in one or more higher layers of the CNN. The outputs of neurons of one or more fully connected layers (e.g., a final layer of an ANN or CNN) could be used to determine information about portions of an input or for the input as a whole.

Neurons in a CNN can be organized according to corresponding dimensions of the input. For example, where the input is a time series of census data (a one-dimensional input), neurons of the CNN (e.g., of an input layer of the CNN, of a pooling layer of the CNN) could correspond to points or periods of time along the one-dimensional input. Connections between neurons and/or filters in different layers of the CNN could be related to such times. For example, a neuron in a convolutional layer of the CNN could receive an input that is based on a convolution of a filter with a portion of the input, or with a portion of some other layer of the CNN, that is at a time proximate to the location of the convolutional-layer neuron. In another example, a neuron in a pooling layer of the CNN could receive inputs from neurons, in a layer higher than the pooling layer (e.g., in a convolutional layer, in a higher pooling layer), that have locations that are proximate to the location of the pooling-layer neuron.

Figure 7:
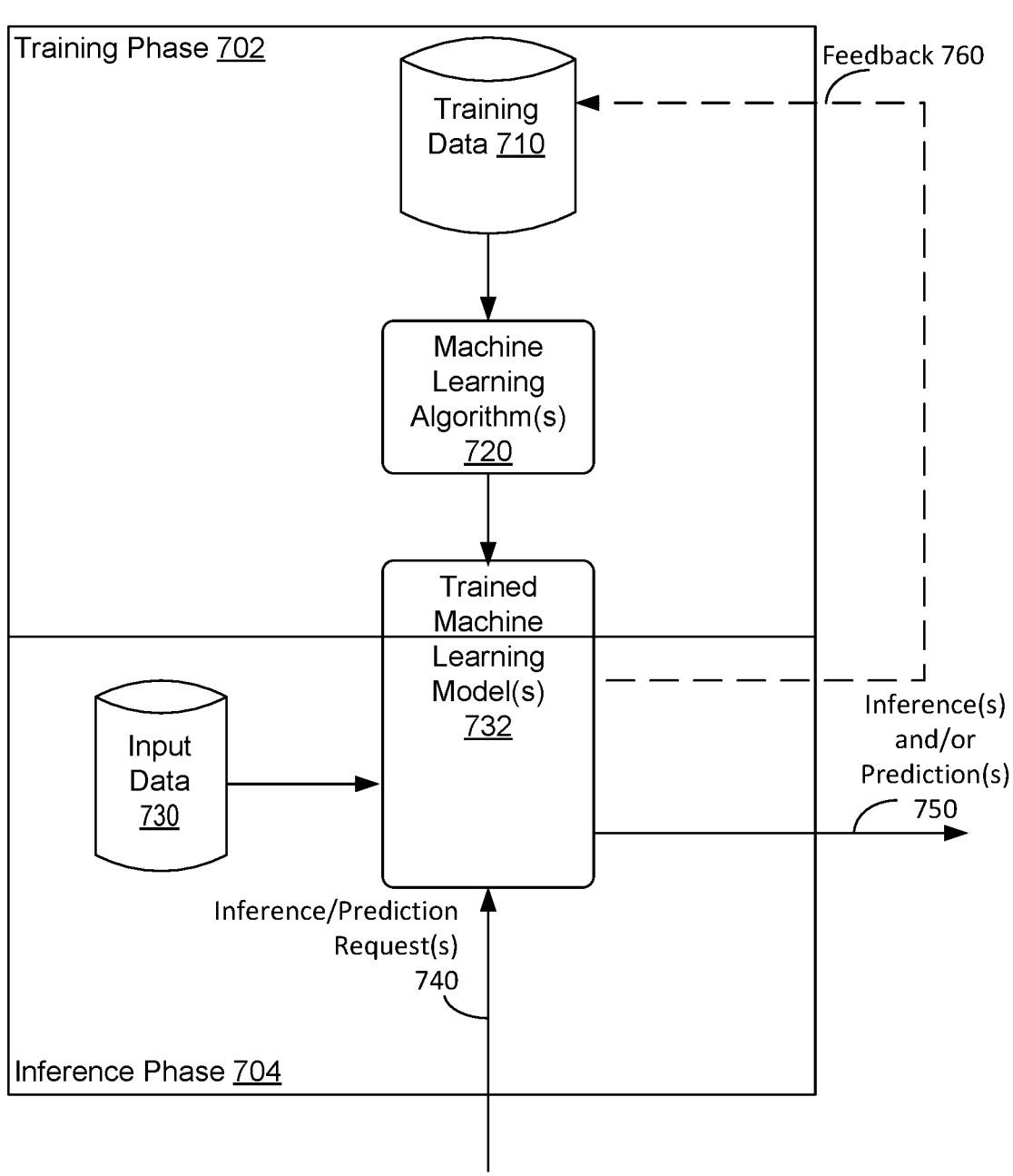
FIG. 7 is a diagram illustrating training and inference phases of a machine learning model, in accordance with example embodiments.

FIG. 7 shows diagram 700 illustrating a training phase 702 and an inference phase 704 of trained machine learning model(s) 732, in accordance with example embodiments. Some machine learning techniques involve training one or more machine learning algorithms, on an input set of training data to recognize patterns in the training data and provide output inferences and/or predictions about (patterns in the) training data. Such output could take the form of filtered or otherwise modified versions of the input, e.g., an input time series of census or other data could be modified by the machine learning model. The resulting trained machine learning algorithm can be termed as a trained machine learning model. For example, FIG. 7 shows training phase 702 where one or more machine learning algorithms 720 are being trained on training data 710 to become trained machine learning model 732. Then, during inference phase 704, trained machine learning model 732 can receive input data 730 and one or more inference/prediction requests 740 (perhaps as part of input data 730) and responsively provide as an output one or more inferences and/or predictions 750.

As such, trained machine learning model(s) 732 can include one or more models of one or more machine learning algorithms 720. Machine learning algorithm(s) 720 may include, but are not limited to: an artificial neural network (e.g., a herein-described convolutional neural networks, a recurrent neural network, a Bayesian network, a hidden Markov model, a Markov decision process, a logistic regression function, a support vector machine, a suitable statistical machine learning algorithm, and/or a heuristic machine learning system), a support vector machine, a regression tree, an ensemble of regression trees (also referred to as a regression forest), a decision tree, an ensemble of decision trees (also referred to as a decision forest), or some other machine learning model architecture or combination of architectures. Machine learning algorithm(s) 720 may be supervised or unsupervised, and may implement any suitable combination of online and offline learning.

In some examples, machine learning algorithm(s) 720 and/or trained machine learning model(s) 732 can be accelerated using on-device coprocessors, such as graphic processing units (GPUs), tensor processing units (TPUs), digital signal processors (DSPs), and/or application specific integrated circuits (ASICs). Such on-device coprocessors can be used to speed up machine learning algorithm(s) 720 and/or trained machine learning model(s) 732. In some examples, trained machine learning model(s) 732 can be trained, reside and execute to provide inferences on a particular computing device, and/or otherwise can make inferences for the particular computing device.

During training phase 702, machine learning algorithm(s) 720 can be trained by providing at least training data 710 as training input using unsupervised, supervised, semi-supervised, and/or reinforcement learning techniques. Unsupervised learning involves providing a portion (or all) of training data 710 to machine learning algorithm(s) 720 and machine learning algorithm(s) 720 determining one or more output inferences based on the provided portion (or all) of training data 710. Supervised learning involves providing a portion of training data 710 to machine learning algorithm(s) 720, with machine learning algorithm(s) 720 determining one or more output inferences based on the provided portion of training data 710, and the output inference(s) are either accepted or corrected based on correct results associated with training data 710. In some examples, supervised learning of machine learning algorithm(s) 720 can be governed by a set of rules and/or a set of labels for the training input, and the set of rules and/or set of labels may be used to correct inferences of machine learning algorithm(s) 720.

Once training phase 702 has been completed, trained machine learning model(s) 732 can be provided to a computing device, if not already on the computing device. Inference phase 704 can begin after trained machine learning model(s) 732 are provided to a computing device.

During inference phase 704, trained machine learning model(s) 732 can receive input data 730 and generate and output one or more corresponding inferences and/or predictions 750 about input data 730. As such, input data 730 can be used as an input to trained machine learning model(s) 732 for providing corresponding inference(s) and/or prediction(s) 750 to kernel components and non-kernel components. For example, trained machine learning model(s) 732 can generate inference(s) and/or prediction(s) 750 in response to one or more inference/prediction requests 740. In some examples, trained machine learning model(s) 732 can be executed by a portion of other software. For example, trained machine learning model(s) 732 can be executed by an inference or prediction daemon to be readily available to provide inferences and/or predictions upon request. Input data 730 can include data from a computing device executing trained machine learning model(s) 732 and/or input data from one or more computing devices other than the executing device.

IV. ILLUSTRATIVE SYSTEMS

Figure 8:
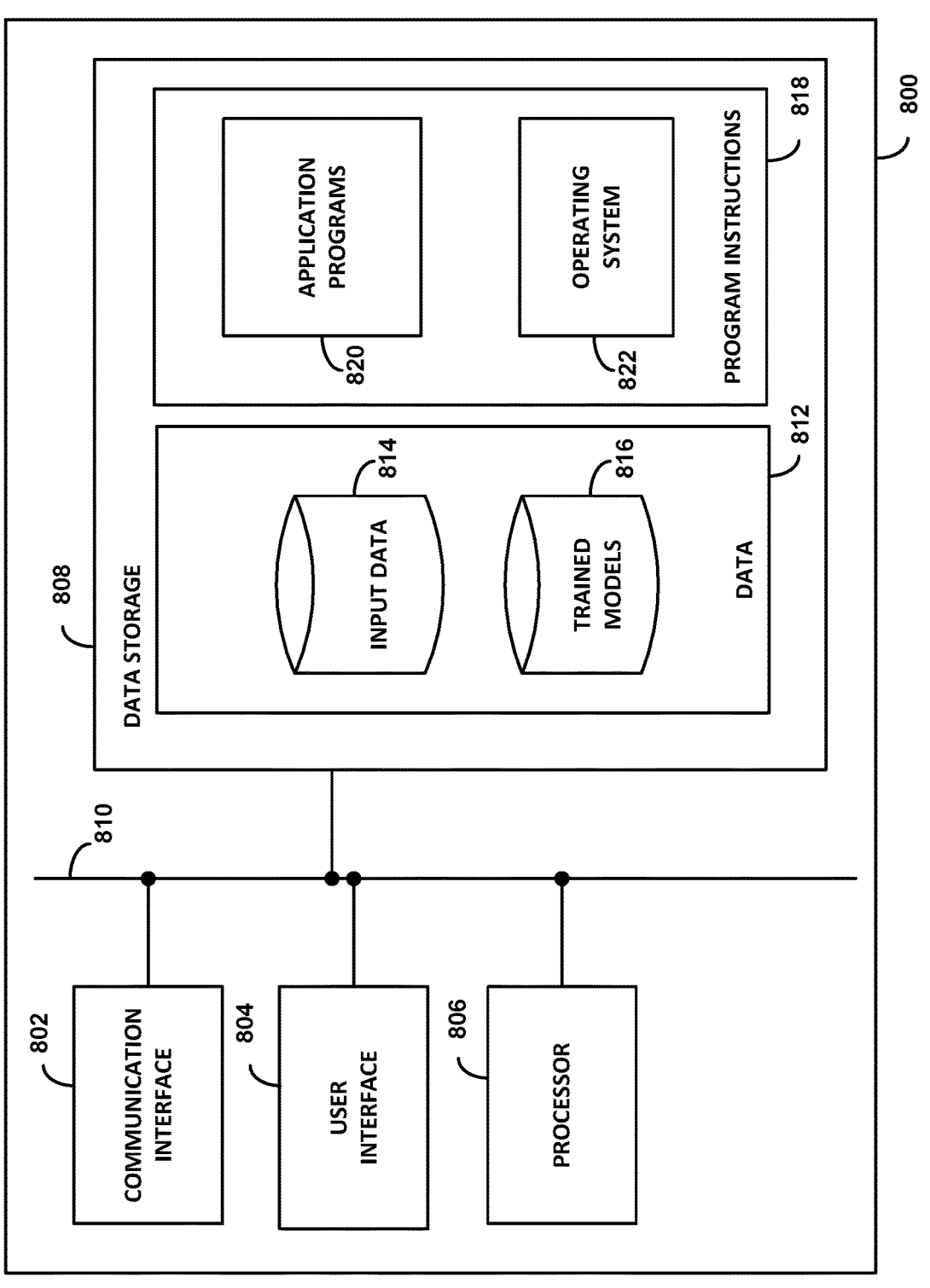
FIG. 8 is a simplified block diagram showing some of the components of an example computing system.

FIG. 8 illustrates an example computing device 800 that may be used to implement the methods described herein. By way of example and without limitation, computing device 800 may be a cellular mobile telephone (e.g., a smartphone), a computer (such as a desktop, notebook, tablet, or handheld computer, a server), elements of a cloud computing system, or some other type of device. It should be understood that computing device 800 may represent a physical computing device such as a server, a particular physical hardware platform on which a prediction and/or scheduling application operates in software, or other combinations of hardware and software that are configured to carry out functions as described herein.

As shown in FIG. 8, computing device 800 may include a communication interface 802, a user interface 804, a processor 806, and data storage 808, all of which may be communicatively linked together by a system bus, network, or other connection mechanism 310.

Communication interface 802 may function to allow computing device 800 to communicate, using analog or digital modulation of electric, magnetic, electromagnetic, optical, or other signals, with other devices, access networks, and/or transport networks. Thus, communication interface 802 may facilitate circuit-switched and/or packet-switched communication, such as plain old telephone service (POTS) communication and/or Internet protocol (IP) or other packetized communication. For instance, communication interface 802 may include a chipset and antenna arranged for wireless communication with a radio access network or an access point. Also, communication interface 802 may take the form of or include a wireline interface, such as an Ethernet, Universal Serial Bus (USB), or High-Definition Multimedia Interface (HDMI) port. Communication interface 802 may also take the form of or include a wireless interface, such as a Wi-Fi, BLUETOOTH®, global positioning system (GPS), or wide-area wireless interface (e.g., WiMAX or 3GPP Long-Term Evolution (LTE)). However, other forms of physical layer interfaces and other types of standard or proprietary communication protocols may be used over communication interface 802. Furthermore, communication interface 802 may comprise multiple physical communication interfaces (e.g., a Wi-Fi interface, a BLUETOOTH® interface, and a wide-area wireless interface).

In some embodiments, communication interface 802 may function to allow computing device 800 to communicate, with other devices, remote servers, access networks, and/or transport networks. For example, the communication interface 802 may function to access one or more machine learning models or other predictive algorithms and/or input therefor via communication with a remote server or other remote device or system in order to allow the computing device 800 to use the machine learning model or algorithms to generate outputs (e.g., predicted information about census, available FTEs, staff schedules, or other information related to the operation of a healthcare facility) based on input data. For example, the computing system 800 could be a medical records server and the remote system could be a smartphone via which a staff member accesses and/or interacts with a work schedule.

User interface 804 may function to allow computing device 800 to interact with a user, for example to receive input from and/or to provide output to the user. Thus, user interface 804 may include input components such as a keypad, keyboard, touch-sensitive or presence-sensitive panel, computer mouse, trackball, joystick, microphone, and so on. User interface 804 may also include one or more output components such as a display screen which, for example, may be combined with a presence-sensitive panel. The display screen may be based on CRT, LCD, and/or LED technologies, or other technologies now known or later developed. User interface 804 may also be configured to generate audible output(s), via a speaker, speaker jack, audio output port, audio output device, earphones, and/or other similar devices.

Processor 806 may comprise one or more general purpose processors—e.g., microprocessors—and/or one or more special purpose processors—e.g., digital signal processors (DSPs), graphics processing units (GPUs), floating point units (FPUs), network processors, tensor processing units (TPUs), or application-specific integrated circuits (ASICs). In some instances, special purpose processors may be capable of executing artificial neural networks, executing convolutional neural networks, or executing some other predictive models or algorithms among other applications or functions. Data storage 808 may include one or more volatile and/or non-volatile storage components, such as magnetic, optical, flash, or organic storage, and may be integrated in whole or in part with processor 806. Data storage 808 may include removable and/or non-removable components.

Processor 806 may be capable of executing program instructions 818 (e.g., compiled or non-compiled program logic and/or machine code) stored in data storage 808 to carry out the various functions described herein. Therefore, data storage 808 may include a non-transitory computer-readable medium, having stored thereon program instructions that, upon execution by computing device 800, cause computing device 800 to carry out any of the methods, processes, or functions disclosed in this specification and/or the accompanying drawings. The execution of program instructions 818 by processor 806 may result in processor 806 using data 812.

By way of example, program instructions 818 may include an operating system 822 (e.g., an operating system kernel, device driver(s), and/or other modules) and one or more application programs 820 (e.g., functions for executing trained machine learning models and/or other predictive or scheduling methods as described herein) installed on computing device 800. Data 812 may include census data, ADT data, staff schedule or availability data, or some other input 814 and/or one or more trained machine learning models 816 or other elements of a predictive method as described herein (e.g., weights for combining the outputs of a number of different predictive models, be they machine learning models or other varieties of model). Input data 814 may be used to train predictors (e.g., machine learning models thereof) and/or may be applied to such a predictor in order to generate a staff work schedule, to predict census data, to predict long-term staffing and patient load, or to generate some other output as described herein.

Application programs 820 may communicate with operating system 822 through one or more application programming interfaces (APIs). These APIs may facilitate, for instance, application programs 820 reading and/or writing a trained predictive model 816, transmitting or receiving information via communication interface 802, receiving and/or displaying information on user interface 804, and so on.

Application programs 820) may take the form of "apps" that could be downloadable to computing device 800 through one or more online application stores or application markets (via, e.g., the communication interface 802). However, application programs can also be installed on computing device 300 in other ways, such as via a web browser or through a physical interface (e.g., a USB port) of the computing device 800.

VI. CONCLUSION

The above detailed description describes various features and functions of the disclosed systems, devices, and methods with reference to the accompanying figures. In the figures, similar symbols typically identify similar components, unless the context indicates otherwise. The illustrative embodiments described in the detailed description, figures, and claims are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the message flow diagrams, scenarios, and flowcharts in the figures and as discussed herein, each step, block and/or communication may represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages may be executed out of order from that shown or discussed, including in substantially concurrent or in reverse order, depending on the functionality involved. Further, more or fewer steps, blocks and/or functions may be used with any of the message flow diagrams, scenarios, and flow charts discussed herein, and these message flow diagrams, scenarios, and flow charts may be combined with one another, in part or in whole.

A step or block that represents a processing of information may correspond to circuitry that can be configured to perform the specific logical functions of a herein-described method or technique. Alternatively or additionally, a step or block that represents a processing of information may correspond to a module, a segment, or a portion of program code (including related data). The program code may include one or more instructions executable by a processor for implementing specific logical functions or actions in the method or technique. The program code and/or related data may be stored on any type of computer-readable medium, such as a storage device, including a disk drive, a hard drive, or other storage media.

The computer-readable medium may also include non-transitory computer-readable media such as computer-readable media that stores data for short periods of time like register memory, processor cache, and/or random access memory (RAM). The computer-readable media may also include non-transitory computer-readable media that stores program code and/or data for longer periods of time, such as secondary or persistent long term storage, like read only memory (ROM), optical or magnetic disks, and/or compact-disc read only memory (CD-ROM), for example. The computer-readable media may also be any other volatile or non-volatile storage systems. A computer-readable medium may be considered a computer-readable storage medium, for example, or a tangible storage device.

Moreover, a step or block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

We claim:

1. A method, comprising:

obtaining census data indicative of patient census across a first time period at a first temporal resolution;

generating a regression model to predict the census data as a function of time at the first temporal resolution;

applying the regression model to generate a first predicted dataset that predicts the patient census across the first time period at the first temporal resolution;

applying a trained layered artificial neural network (LANN) and a trained long short term memory artificial neural network (LSTM) to predict, at the first temporal resolution, forward-looking periods of the census data based on corresponding backward-looking periods of the census data;

determining weights to linearly combine outputs of the regression model, the LANN, and the LSTM to predict the census data;

applying the regression model to generate a second predicted dataset that predicts, at the first temporal resolution, the patient census across a second time period that is subsequent to the first time period;

applying the LANN and the LSTM to generate, based on the second predicted dataset, respective third and fourth predicted datasets that predict, at the first temporal resolution, the patient census across the second time period;

linearly combining the second, third, and fourth predicted datasets according to the weights to generate a fifth predicted dataset that predicts, at the first temporal resolution, the patient census across the second time period;

determining, based on the fifth predicted dataset, that at least one additional healthcare provider is likely to be required for a third time period within the second time period;

receiving, from a remote system, a request for the availability of a work shift during a request period that includes the third time period; and based on determining that at least one additional healthcare provider is likely to be required for a third time period and responsive to receiving the request, sending to the remote system an indication that a work shift is available during the third time period.

2. The method of claim 1, further comprising:

subsequent to sending the indication that a work shift is available during the third time period to the remote system, obtaining updated census data;

updating the regression model, LANN, LSTM, and weights based on the updated census data;

applying the updated regression model, updated LANN, updated LSTM, and updated weights to generate a sixth predicted dataset that predicts, at the first temporal resolution, the patient census across the second time period;

determining, based on the sixth predicted dataset, that at least one additional healthcare provider is unlikely to be required for the third time period within the second time period;

receiving, from the remote system, an additional request for the availability of a work shift during an additional request period that includes the third time period; and based on determining that at least one additional healthcare provider is unlikely to be required for the third time period and responsive to receiving the additional request, sending to the remote system an indication that a work shift is not available during the third time period.

3. The method of claim 1, wherein the regression model includes (i) at least one term related to an overall trend of the patient census over time, and (ii) one or more terms related to at least one of: day of the week, day of the year, season, month, holiday status, holiday identity, hour of the day, or shift of the day.

4. The method of claim 1, wherein determining, based on the fifth predicted dataset, that at least one additional healthcare provider is likely to be required for the third time period within the second time period comprises:

applying a stochastic predictor to the fifth predicted dataset to generate a plurality of simulated patient censuses; and based on the plurality of simulated patient censuses, determining a schedule of the number of healthcare providers likely to be required across the second time period.

5. The method of claim 4, wherein applying the stochastic predictor to the fifth predicted dataset to generate a plurality of simulated patient censuses comprises:

determining, based on the fifth predicted dataset, a trend in the patient census across at least the second time period;

determining, across at least the second time period, one or more predicted patient admission rates into at least one department of a healthcare facility based on at least the determined trend in the patient census across at least the second time period; and based on at least the one or more predicted patient admission rates, generating a plurality of simulated patient censuses by simulating the entry and exit of patients into and out of the at least one department of the healthcare facility.

6. The method of claim 4, wherein determining, based on the plurality of simulated patient censuses, the schedule of the number of healthcare providers likely to be required across the second time period comprises reducing an expected level of a cost function across the plurality of patient censuses.

7. The method of claim 4, wherein determining, based on the plurality of simulated patient censuses, the schedule of the number of healthcare providers likely to be required across the second time period comprises determining the schedule of the number of healthcare providers likely to be required across the second time period based on data about at least one of an anticipated amount or pattern of paid time off available during the second time period, an anticipated amount or pattern of healthcare worker vacancies during the second time period, or an anticipated amount or pattern of healthcare worker medical leave during the second time period.

8. The method of any of claim 4, wherein determining, based on the plurality of simulated patient censuses, the schedule of the number of healthcare providers likely to be required across the second time period comprises determining a schedule of core healthcare staff at a resolution greater than twice per day and determining a schedule of float healthcare staff at a resolution greater than twice per month.

9. The method of claim 1, wherein the trained LANN comprises a convolutional neural network, and wherein applying the trained LANN and trained LSTM to predict, at the first temporal resolution, forward-looking periods of the census data comprises applying (i) the corresponding backward-looking periods of the census data and (ii) the first predicted dataset to the trained LANN and to the trained LSTM.

10. The method of claim 1, wherein the trained LANN comprises a recurrent neural network, wherein the method further comprises:

applying a short fast Fourier transform (SFFT) to predict, at the first temporal resolution, forward-looking periods of the census data based on corresponding backward-looking periods of the census data, wherein determining weights to linearly combine outputs of the regression model, the LANN, and the LSTM to predict the census data comprises determining weights to linearly combine outputs of the regression model, the LANN, the LSTM, and the SFFT to predict the census data;

applying the SFFT to generate, based on the second predicted dataset, a seventh predicted dataset that predicts, at the first temporal resolution, the patient census across the second time period, wherein linearly combining the second, third, and fourth predicted datasets according to the weights to generate a fifth predicted dataset comprises linearly combining the second, third, fourth, and seventh predicted datasets according to the weights to generate the fifth predicted dataset.

11. A method, comprising:

obtaining census data indicative of patient census across a first time period at a first temporal resolution;

generating a regression model to predict the census data as a function of time at the first temporal resolution;

applying the regression model to generate a first predicted dataset that predicts the patient census across the first time period at the first temporal resolution;

applying a trained layered artificial neural network (LANN) and a trained long short term memory artificial neural network (LSTM) to predict, at the first temporal resolution, forward-looking periods of the census data based on corresponding backward-looking periods of the census data;

determining weights to linearly combine outputs of the regression model, the LANN, and the LSTM to predict the census data;

applying the regression model to generate a second predicted dataset that predicts, at the first temporal resolution, the patient census across a second time period that is subsequent to the first time period;

applying the LANN and the LSTM to generate, based on the second predicted dataset, respective third and fourth predicted datasets that predict, at the first temporal resolution, the patient census across the second time period;

linearly combining the second, third, and fourth predicted datasets accordingly to the weights to generate a fifth predicted dataset that predicts, at the first temporal resolution, the patient census across the second time period;

determining, based on the fifth predicted dataset, a work schedule for a healthcare provider;

providing, via a user interface, an indication of the work schedule;

receiving, via the user interface, an indication of an update to the work schedule; and receiving, via the user interface, an indication of an approval of the work schedule as updated according to the indicated update.

12. The method of claim 11, further comprising:

receiving, from a remote system subsequent to receiving the indication of the approval of the work schedule as updated according to the indicated update, a request for a work schedule for the healthcare worker; and responsive to receiving the request, sending to the remote system an indication of the work schedule as updated according to the indicated update.

13. The method of any of claim 11, wherein determining, based on the fifth predicted dataset, the work schedule for the healthcare provider comprises:

determining, based on the fifth predicted dataset, a trend in the patient census across at least the second time period;

determining, across at least the second time period, one or more predicted patient admission rates into at least one department of a healthcare facility based on at least the determined trend in the patient census across at least the second time period;

based on at least the one or more predicted patient admission rates, generating a plurality of simulated patient censuses by simulating the entry and exit of patients into and out of the at least one department of the healthcare facility; and based on the plurality of simulated patient censuses, determining a schedule of the number of healthcare providers likely to be required across the second time period.

14. The method of claim 11, wherein the trained LANN comprises a recurrent neural network, wherein the method further comprises:

applying a short fast Fourier transform (SFFT) to predict, at the first temporal resolution, forward-looking periods of the census data based on corresponding backward-looking periods of the census data, wherein determining weights to linearly combine outputs of the regression model, the LANN, and the LSTM to predict the census data comprises determining weights to linearly combine outputs of the regression model, the LANN, the LSTM, and the SFFT to predict the census data;

applying the SFFT to generate, based on the second predicted dataset, a seventh predicted dataset that predicts, at the first temporal resolution, the patient census across the second time period, wherein linearly combining the second, third, and fourth predicted datasets according to the weights to generate a fifth predicted dataset comprises linearly combining the second, third, fourth, and seventh predicted datasets according to the weights to generate the fifth predicted dataset.

15. The method of claim 1, wherein applying the regression model to generate a second predicted dataset comprises applying the regression model to generate a sixth predicted dataset that predicts, at the first temporal resolution, the patient census across a fourth time period that is a subset of the second time period and a seventh predicted dataset that predicts, at the first temporal resolution, the patient census across a fifth time period that is a subset of the second time period and that is subsequent to the fifth time period, wherein applying the LANN and the LSTM to generate, based on the second predicted dataset, respective third and fourth predicted datasets comprises applying the LANN and the LSTM to generate, based on the sixth predicted dataset, respective eighth and ninth predicted datasets that predict, at the first temporal resolution, the patient census across the fifth time period, and wherein linearly combining the second, third, and fourth predicted datasets according to the weights to generate a fifth predicted dataset comprises linearly combining the seventh, eighth, and ninth predicted datasets according to the weights to generate a tenth predicted dataset that predicts, at the first temporal resolution, the patient census across the fifth time period.

16. The method of claim 15, wherein applying the LANN and the LSTM to generate, based on the sixth predicted dataset, respective eighth and ninth predicted datasets comprises applying the LANN and the LSTM to generate, based on the sixth and seventh predicted datasets, the respective eighth and ninth predicted datasets, and wherein applying the trained LANN and trained LSTM to predict, at the first temporal resolution, forward-looking periods of the census data comprises applying (i) the corresponding backward-looking periods of the census data and (ii) the first predicted dataset to the trained LANN and to the trained LSTM.

17. The method of claim 15, wherein the trained LANN comprises a recurrent neural network, and wherein the method further comprises:

applying a short fast Fourier transform (SFFT) to predict, at the first temporal resolution, forward-looking periods of the census data based on corresponding backward-looking periods of the census data, wherein determining weights to linearly combine outputs of the regression model, the LANN, and the LSTM to predict the census data comprises determining weights to linearly combine outputs of the regression model, the LANN, the LSTM, and the SFFT to predict the census data;

applying the SFFT to generate, based on the sixth predicted dataset, an eleventh predicted dataset that predicts, at the first temporal resolution, the patient census across the fifth time period, wherein linearly combining the second, third, and fourth predicted datasets according to the weights to generate a fifth predicted dataset comprises linearly combining the seventh, eighth, ninth, eleventh predicted datasets according to the weights to generate the tenth predicted dataset.

18. The method of claim 15, wherein the method further comprises:

applying the LANN and the LSTM to generate respective eleventh and twelfth predicted datasets that predict, at the first temporal resolution, the patient census across the fourth time period; and linearly combining the sixth, eleventh, and twelfth predicted datasets according to the weights to generate a thirteenth predicted dataset that predicts, at the first temporal resolution, the patient census across the fourth time period, wherein applying the LANN and the LSTM to generate, based on the sixth predicted dataset, respective eighth and ninth predicted datasets comprises applying the LANN and the LSTM to generate, based on the thirteenth predicted dataset, the respective eighth and ninth predicted datasets.

19. The method of claim 11, wherein applying the regression model to generate a second predicted dataset comprises applying the regression model to generate a sixth predicted dataset that predicts, at the first temporal resolution, the patient census across a fourth time period that is a subset of the second time period and a seventh predicted dataset that predicts, at the first temporal resolution, the patient census across a fifth time period that is a subset of the second time period and that is subsequent to the fifth time period, wherein applying the LANN and the LSTM to generate, based on the second predicted dataset, respective third and fourth predicted datasets comprises applying the LANN and the LSTM to generate, based on the sixth predicted dataset, respective eighth and ninth predicted datasets that predict, at the first temporal resolution, the patient census across the fifth time period, and wherein linearly combining the second, third, and fourth predicted datasets according to the weights to generate a fifth predicted dataset comprises linearly combining the seventh, eighth, and ninth predicted datasets according to the weights to generate a tenth predicted dataset that predicts, at the first temporal resolution, the patient census across the fifth time period.

20. The method of claim 19, wherein applying the LANN and the LSTM to generate, based on the sixth predicted dataset, respective eighth and ninth predicted datasets comprises applying the LANN and the LSTM to generate, based on the sixth and seventh predicted datasets, the respective eighth and ninth predicted datasets, and wherein applying the trained LANN and trained LSTM to predict, at the first temporal resolution, forward-looking periods of the census data comprises applying (i) the corresponding backward-looking periods of the census data and (ii) the first predicted dataset to the trained LANN and to the trained LSTM.

21. The method of claim 19, wherein the method further comprises:

applying the LANN and the LSTM to generate respective eleventh and twelfth predicted datasets that predict, at the first temporal resolution, the patient census across the fourth time period; and linearly combining the sixth, eleventh, and twelfth predicted datasets according to the weights to generate a thirteenth predicted dataset that predicts, at the first temporal resolution, the patient census across the fourth time period, wherein applying the LANN and the LSTM to generate, based on the sixth predicted dataset, respective eighth and ninth predicted datasets comprises applying the LANN and the LSTM to generate, based on the thirteenth predicted dataset, the respective eighth and ninth predicted datasets.

* * * * *